(12) United States Patent
Michetti et al.

(10) Patent No.: US 6,290,962 B1
(45) Date of Patent: *Sep. 18, 2001

(54) UREASE-BASED VACCINE AND TREATMENT FOR HELICOBACTER INFECTION

(75) Inventors: Pierre Michetti; Iréne Corthésy-Theulaz, both of Lausanne; André Blum, Romammôtier; Catherine Davin, Nyon; Rainier Haas, Tübingen; Jean-Pierre Kraehenbuhl, Rivat; Emilia Saraga, Lausanne, all of (CH)

(73) Assignee: OraVax, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/200,346

(22) Filed: Feb. 23, 1994

Related U.S. Application Data

(63) Continuation-in-part of application No. 08/085,938, filed on Jul. 6, 1993, now Pat. No. 5,972,336, which is a continuation-in-part of application No. 07/970,996, filed on Nov. 3, 1992, now abandoned.

(51) Int. Cl.[7] .......................... A61K 39/00; A61K 38/46; A61K 31/70; A61K 39/385

(52) U.S. Cl. .................... 424/185.1; 424/234.1; 424/184.1; 424/192.1; 424/193.1; 424/197.1; 424/261.1; 424/280.1; 424/278.1; 424/94.6; 424/282.1; 424/203.1; 514/41; 514/234.5

(58) Field of Search .................. 424/234.1, 192.1, 424/193.1, 197.11, 261.1, 278.1, 280.1, 185.1, 184.1, 94.6, 282.1, 203.1; 514/41, 234.5

(56) References Cited

U.S. PATENT DOCUMENTS

| | | |
|---|---|---|
| 4,879,213 * | 11/1989 | Fox et al. . |
| 5,403,924 | 4/1995 | Cover et al. .................... 536/23.1 |
| 5,538,729 * | 7/1996 | Czinn et al. . |
| 5,578,302 * | 11/1996 | Brassart et al. . |
| 5,733,740 | 3/1998 | Cover et al. .................... 435/7.32 |
| 5,859,219 | 1/1999 | Cover et al. .................... 536/22.1 |
| 5,871,749 | 2/1999 | Doidge et al. ................... 424/234.1 |
| 5,972,336 * | 10/1999 | Michetti et al. . |
| 5,985,631 * | 11/1999 | Soman et al. . |
| 6,060,241 * | 5/2000 | Corthésy-Theulaz . |
| 6,096,521 * | 8/2000 | Haas et al. . |

FOREIGN PATENT DOCUMENTS

| | | |
|---|---|---|
| WO A 91/16072 | 10/1991 | (WO) . |
| WO 93/16723 | 2/1993 | (WO) . |
| WO 94/09823 | 11/1994 | (WO) . |
| WO 95/03824 | 2/1995 | (WO) . |

OTHER PUBLICATIONS

Solnick et al, Infection and Immunity 68/5: 2560–565, 2000.*

Corthésy-Theulaz et al, Gastroenterology 109: 115–121, 1995.*

Sutton et al, Vaccine 18: 2677–2685, 2000.*

Weltzin et al, Injection and Immunity 68/5: 2775–782 2000.*

Michetti et al, Gastroenterology 116: 804–812, 1999.*

"Vaccines" (Plotkin, S.A ed) see pp. 570, and 571, published by W.B. Saunders Company, 1988.*

Davin et al., "*H. Pylor* Urease Elicits Protection Against *H. felis*infection in Mice, " Gastroenterology 104: A 1035 (1993).

Ferrero et al., "Recombinant Antigens Prepared from the Urease Subunits of *Helicobacter*spp: Evidence of Protection in a Mouse Model of Gastric Infection, " Infection and Immunity 62: 4981–4989 (1994).

Michetti et al., "Immunization of BALB/c Mice Against *Helicobacter felis*Infection With *Helicobacter pylori*Urease, " Gastroenterolgy 107: 1002–1011 (1994).

Cornelissen et al., Anti–idiotypic Immunization Provides Protection Against Lethal Endotoxaemia in BALB/c Mice, Immunology 79:673–680, 1993.

Isaacson, Pathegenes is and Early Lesions in Extranodal Lymphoma, Toxicology Letters 67:237–247, 1993.

Kingsman and Kingsman, Polyvalent Recombinant Antigens: A New Vaccine Strategy, Vaccine 6:304–306, 1988.

Schmitt et al., Degradation and Release Properties of Pellets Fabricated from Three Commercial Poly(D, L–lactode–c-o–glycolide) Biodegradable Polymers, J. Pharmaceutical Sciences 82:326–329, 1993.

Sobala et al., Levels of Nitrite, Nitrute, N–nitroso Compound, Ascorbic Acid and total Bile Acids in Gastric Juice of Patients With and Without Precancerous Conditions of the Stomach, Carecinogenesis 12:193–198, 1991.

* cited by examiner

Primary Examiner—Nita Mannfield
(74) Attorney, Agent, or Firm—Clark & Elbing LLP

(57) ABSTRACT

Method of eliciting in a mammalian host a protective immune response to Helicobacter infection and treatment of Helicobacter infection by administering to the host an immunogenically effective amount of a Helicobacter urease or urease subunits as antigen. Vaccine compositions are also provided.

72 Claims, 6 Drawing Sheets

UREASE-BASED VACCINE AND TREATMENT FOR HELICOBACTER INFECTION

RELATED APPLICATIONS

This application is a continuation-in-part of U.S. application Ser. No. 08/085,938, filed Jul. 6, 1993 now U.S. Pat. No. 5,972,336, which is a continuation-in-part application of U.S. application Ser. No. 07/970,996, filed Nov. 3, 1992, now abandoned the whole of which applications (including drawings) are hereby incorporated by reference.

The present invention relates to the prevention and treatment of gastric infection in mammals, including humans. More particularly, the present invention relates to a vaccine suitable for use in the prevention and treatment of Helicobacter infection in mammals, including humans, and to a method of treatment of humans suffering from gastric infection, its consequences such as chronic gastritis or peptic ulcer, and prevention of gastric cancer.4

BACKGROUND OF THE INVENTION

Helicobacter infections of human gastric epithelium cause gastritis, are a major factor in the development of peptic ulcers and gastric lymphoma, and may be a risk factor for the development of gastric cancer. (Blaser, M. J. "Gastric Campylobacter-like Organisms, Gastritis and Peptic Ulcer Disease" Gastroenterology, vol. 93, 371–383 (1987); Graham, D. Y. "*Campylobacter pylori* and Peptic Ulcer Disease" Gastroenterology, vol. 196, 615–625 (1989); Parsonnet, J. et al. "*Helicobacter pylori* Infection in Intestinal and Diffuse-Type Gastric Adenocarcinomas" J. Natl. Cancer Inst., vol. 93, 640–643 (1991); Wotherspoon, A. C., et al., "Regression of Primary Low-Grade B-Cell Gastric Lymphoma of Mucosa-Associated Lymphoid Tissue Type After Eradication of *Helicobacter pylori*," Lancet, vol. 342, 575–577 (1993)). The most frequent infection agent is *Helicobacter pylori*, followed at a much lower frequency by *Helicobacter heilmanii*. *Helicobacter pylori* is a slender S-shaped gram negative microorganism, which is routinely recovered from gastric biopsies of adults and children with histologic evidence of gastritis or peptic ulceration. Evidence for a causal elationship between *Helicobacter pylori* and gastroduodenal disease comes from studies in human volunteers, patients with ulcers and gastric cancer, gnotobiotic pigs, and germ-free rodents. Regarding etiology, Koch's postulates were satisfied by creating histologically confirmed gastritis in previously uninfected individuals following consumption of viable microorganisms. (Marshall, B. J. et al. "Attempt to Fulfill Koch's Postulate for pyloric Campylobacter" Med. J. Aust., vol. 142, 436–439 (1985); Morris, A. et al. "Ingestion of *Campylobacter pyloritis* Causes Gastritis and Raised Fasting Gastric pH" Am. J. Gastroenterol., vol. 82, 192–199 (1987); Engstrand, L. et al. "Inoculation of Barrier-Born Pigs With *Helicobacter pylori*: A Useful Animal Model for Gastritis Type B" Infect. Immun., vol. 53, 1763–1768 (1990); Fox, J. G. et al. "Gastric Colonization by *Campylobacter pylori* Subsp. mustelae in Ferrets" Infect. Immun., vol. 56, 2994–2996 (1988); Fox, J. G. et al. "*Helicobacter mustelae*-Associated Gastritis in Ferrets: An Animal Model of *Helicobacter pylori* Gastritis in Humans" Gastroenterology, vol. 99, 352–361 (1990); Lee, A. et al. "A Small Animal Model of Human *Helicobacter pylori* Active Chronic Gastritis" Gastroenterology, vol. 99, 1315–1323 (1990); Fox, J. G. et al. "*Helicobacter Felis* Gastritis in Gnotobiotic Rats: An Animal Model of *Helicobacter pylori* Gastritis" Infect. Immun., vol. 59, 785–791 (1991); Eaton, K. A. et al. "*Campylobacter pylori* Virulence Factors in Gnotobiotic Piglets" Infect. Immun., vol. 57, 1119–1125 (1989)), and by treatment to eradicate *Helicobacter pylori*, with resolution of the gastritis and, in patients with peptic ulcer disease, a decrease in the recurrence rate. (Peterson, W. L. "*Helicobacter pylori* and Peptic Ulcer Disease" N. Engl. J. Med., vol. 324, 1043–1048 (1991)).

Gastroduodenal diseases thought to be associated with Helicobacter infection include acute, chronic, and atrophic gastritis, peptic ulcer disease including both gastric and duodenal ulcers, gastric cancer, chronic dyspepsia with severe erosive gastroduodenitis, refractory non-ulcer dyspepsia, intestinal metaplasia, and low grade MALT lymphoma. Helicobacter infection is also the principle cause of asymptomatic chronic gastritis.

In spite of in vitro susceptibility to many antimicrobial agents, in vivo eradication of established *Helicobacter pylori* infections with antimicrobial agents is often difficult to achieve. (Czinn, S. J. and Nedrud, J. G. "Oral Immunization Against *Helicobacter pylori*" Infect. Immun., vol. 59, 2359–2363 (1991)). The microorganism is found within the mucous coat overlying the gastric epithelium and in gastric pits. These are locations which do not appear to allow for adequate antimicrobial levels to be achieved even when antibiotics are given orally at high doses. At the present time, most authorities recommend a "triple therapy", namely a bismuth salt in combination with drugs such as tetracycline and metronidazole for 2–4 weeks. However, the effectiveness of this or other chemotherapeutic regimens remains suboptimal. Recently, a National Institutes of Health panel of medical experts recommended a triple therapy with bismuth, tetracycline and metronidazole, administered for two weeks for treatment of peptic ulcers (Cimons, M., "Drug Combination Found Effective on Peptic Ulcers," L.A. Times at A14 (Feb. 10, 1994)). However, this treatment is commonly associated with diarrhea and it may produce serious adverse drug reactions. (See, Dick-Hegedus, E. and Lee, A., "Use of a Mouse Model to Examine Anti-Helicobacter pylori Agents," Scand. J. Gastroenterol., vol. 26, 909–915 (1991)). Treatment with antibiotics also may not solve the problem of reinfection and there is evidence for a high incidence of reinfection in some studies (Coelho, L. G., et al., "Duodenal Ulcer and Eradication of H. pylori in a Developing Country: An 18-Month Follow-Up Study," Scand. J. Gastroenterol. vol. 27, 362–66 (1992)). Therefore there is a great need for a vaccine that can be used to treat infection and to prevent future infections.

At the present time little is known regarding the role of the mucosal immune systems in the stomach. The distribution of immunoglobulin (Ig) producing cells in the normal gastric antrum indicates that IgA plasma cells make up 80% of the total plasma cell population. In addition, the number of plasma IgA cells present in the gastric antrum is comparable to other mucus membranes. (Brandtzaeg, P. "Role of J Chain and Secretory Component in Receptor-Mediated Glandular and Hepatic Transport of Immunoglobulins in Man" Scand. J. Immunol., vol. 22, 111–146 (1985); Brandtzaeg, P. et al. "Production and Secretion of Immunoglobulins in the Gastrointestinal Tract" Ann. Allergy, vol. 59, 21–39 (November, 1987)). A number of studies in humans (Wyatt, J. I. et al. "Local Immune Response to Gastritis Campylobacter in Non-ulcer Dyspepsia" J. Clin. Path., vol. 39, 863–870 (1986)), and in animal models (Fox, J. G. et al. "*Helicobacter mustelae*-Associated Gastritis in Ferrets: An Animal Model of *Helicobacter pylori* Gastritis in Humans" Gastroenterology, vol. 99, 352–361 (1990); Fox, J. G. et al.

"Helicobacter felis Gastritis in Gnotobiotic Rats: An Animal Model of Helicobacter pylori Gastritis" Infect. Immun., vol. 59, 785–791 (1991); Fox, J. G. et al. "Local and Systemic Immune Responses in Murine Helicobacter felis Active Chronic Gastritis," Infect. & Immun., vol. 61, 2309–15 (1993)), have demonstrated specific IgG and IgA responses in serum and in gastric secretions in response to Helicobacter infection. However, the observation that Helicobacter pylori infection persists as a chronic infection for years, despite inducing a local and systemic immune response, is not encouraging the development of immunization strategies.

Lee et al. have reported the ability to infect germ-free rodents with Helicobacter felis, a bacterium closely related to Helicobacter pylori, and reproducibly document histologic gastritis. (Lee, A. et al. "A Small Animal Model of Human Helicobacter pylori Active Chronic Gastritis" Gastroenterology, vol. 99, 1315–1323 (1990); Fox, J. G. et al. "Helicobacter felis Gastritis in Gnotobiotic Rats: An Animal Model of Helicobacter pylori Gastritis" Infect. Immun., vol. 59, 785–791 (1991)). Since then, this bacterium-host pairing has been accepted as a good model to study Helicobacter-mediated gastritis and its initiating factors. (Lee, A. et al. "Pathogenicity of Helicobacter pylori: A Perspective" Infect. Immun., vol. 61, 1601–1610 (1993)). Infection of mice with H. felis results in a similar pathologic response to that found in humans infected with H. pylori; both types of infections result in active, chronic gastritis. (Lee et al., Gastroenterology, vol. 99, pp. 1315–1323 (1990)). Researchers have found that Helicobacter felis has the same susceptibility to antimicrobial therapy as Helicobacter pylori, and the H. felis/mouse model has been used to develop new treatments against H. pylori infection. (Dick-Hegedus, E. and Lee, A., "Use of a Mouse Model to Examine Anti-Helicobacter pylori Agents," Scand. J. Gastroenterol., vol. 26, 909–915 (1991); Chen et al., "Immunization Against Gastric Helicobacter Infection in a Mouse/Helicobacter felis Model," Lancet, vol. 339, p.1120 (1992)). Czinn et al. have shown that repetitive oral immunization with a crude lysate of Helicobacter pylori plus cholera toxin adjuvant induces a vigorous gastrointestinal IgA anti-Helicobacter pylori response in mice and ferrets. (Czinn, S. J. and Nedrud, J. G. "Oral Immunization Against Helicobacter pylori" Infect. Immun., vol. 59, 2359–2363 (1991)). In addition, Chen et al. and Czinn et al. have recently reported that oral immunization with a crude lysate of H. felis induced protection against H. felis infection in mice. (Chen, et al. "Immunization Against Gastric Helicobacter Infection in a Mouse/Helicobacter felis Model," (letter) Lancet, vol. 339,1120–1121 (1992); Czinn, S. et al. "Oral Immunization Protects Germ-Free Mice Against Infection from Helicobacter felis" Proceedings of the DDW, American Gastroenterological Association, 1321, A-331 (May 10–13, 1992); Czinn et al., Vaccine, vol. 11, 637–42 (1993)). The exact nature of the antigen(s) responsible for the induction of this protection, however, had not been determined, and no information suggested that the protective antigen(s) of H. felis that induced protection against this pathogen would induce a cross-reactive protection extending to another Helicobacter species.

We have demonstrated for the first time that Helicobacter pylori and H.felis shared antigenic determinants by obtaining monoclonal antibodies after oral immunization of mice with either Helicobacter pylori or H. felis sonicates and showing that some of these antibodies, directed against Helicobacter pylori, would crossreact with H. felis and vice versa, (Michetti, P. et al. "Specificity of Mucosal IgA Response in Balb/C Mice Following H. felis or Helicobacter pylori Challenges" Proceedings of the DDW, American Gastroenterological Association, 1001, A-251 (May 10–13, 1992); Davin, C. et al. "Helicobacter pylori Urease Elicits Protection Against H. felis Infection in Mice" Proceedings of the DDW, American Gastroenterological Association, 1213, A-304 (May 16–19, 1993)), but the basis for these cross-reactivities were unknown.

Based on the homology existing between the different known urease amino acid sequences, it has been proposed that jack bean urease could be used as a vaccine against Helicobacter pylori. (Pallen, M. J. and Clayton, C. L. "Vaccination Against Helicobacter pylori Urease" Lancet, vol. 336, 186–7 (1990)). Nevertheless, despite the homology among the different urease sequences, cross-reactivity is not the rule. Guo and Liu have shown years ago that ureases of Proteus mirabilis, Proteus vulgaris and Providencia rettqeri show cross-reactivity to each other, while ureases of jack bean and Morcanella morganii are immunologically distinct from the three former ureases. (Guo, M. and Liu, P. V. "Serological Specificities of Ureases of Proteus Species" J. Gen. Microbiol, vol. 136, 1995–2000 (1965)). So, even if an antigenic cross-reactivity of Helicobacter pylori urease with other Helicobacter ureases was a reasonable postulate, no data existed demonstrating that this was really the case until we showed that some H.filis monoclonal antibodies cross-reacted with Helicobacter pylori urease. (Davin, C. et al. "Helicobacter pylori Urease Elicits Protection Against H. felis Infection in Mice" Proceedings of the DDW, American Gastroenterological Association 1213, A-304 (May 16–19, 1993)). J. Pappo has further demonstrated that mice which have been infected by H. felis produce antibodies which crossreact with Helicobacter pylori urease but not jack bean urease (J. Pappo, unpublished data, 1993). The fact that jack bean urease does not fall in the same immunological category than Helicobacter urease suggests that jack bean urease may not be useful for immunization against Helicobacter infections, the way it was done for enteric bacteria. (Pimentel, J. L. and Cook, M. E. "Improved Growth in the Progeny of Hens Immunized with Jackbean Urease" Poultry Sci., vol. 64, 434–439 (1988)). Furthermore, attempts to immunize mice against H. felis infection by oral or intraperitoneal delivery of jack bean urease resulted in the production of antibodies against jack bean urease, but failed to protect the mice from infection. (Chen, M. et al. "Failure of Immunization Against Helicobacter Using Jack Bean Urease," Acta Gastroenterol. Belg., vol. 56, 94 (1993)).

The use of an antigen that is the reaction product of urease and glutaraldehyde is described in U.S. Pat. No. 4,837,017, "Urease Antigen Product and Process," issued Jun. 6, 1989, to LeVeen et al. The patent describes the use of the antigen to reduce ammonia toxicity caused by urea splitting organisms. LeVeen et al. disclose the injection of glutaral-dehyde treated jack bean urease into the bloodstream. The LeVeen patent does not disclose the administration of the urease antigen to the mucosal surface of a mammal in order to stimulate antibody production by the local immune system. Furthermore, there is no evidence in the specification that the injection of a jack bean urease antigen could prevent Helicobacter infection or be used to treat gastroduodenal infection by Helicobacter.

Eaton et al. have shown that mutant H. pylori cultures with weak urease activity are unable to infect gnotobiotic piglets. (Eaton et al., "Essential Role of Urease in the Pathogenesis of Gastritis Induced by Helicobacter pylori in Gnotobiotic Piglets," Gastroenterology, vol. 98, A654 (1990)). Eaton does not describe the use of a urease antigen as a vaccine to prevent Helicobacter infection or as a method of treating Helicobacter infection.

The use of *Helicobacter pylori* urease, or of related ureases, as a vaccine against *Helicobacter pylori* infection has previously been proposed by A. Labigne, and incorporated among the claims of a patent filed on Oct. 6th, 1988 by Pasteur Institute, Paris, France. (Labigne, A. "Sequences of Nucleotides Coding for a Protein Having an Urease Activity". EPO patent application # EPO 367 644 A1, 1989. International Publication # WO 90/04030, 1990). The specification of this document contains, however, no evidence of vaccination of any mammal against any Helicobacter infection with urease. This part of the Pasteur Institute patent, therefore, has not been reduced to practice, and the related claims (claims 27 and 28, page 16) should not be considered as valid. Furthermore, the claims of this document relate to a protein presenting a urease activity, and it will be understood from the experiments described below that enzymatic activity of the urease-based vaccine is not required to induce protection after oral immunization.

Moreover, while sequence homology with other bacterial ureases might support the use of urease as a vaccine candidate against *Helicobacter pylori* infection, the current knowledge of human *Helicobacter pylori* infection would certainly not. First, despite the fact that infected individuals often mount a strong antibody response to urease, the anti-urease immune response does not result in clearance or control of the infection. Second, *Helicobacter pylori* is able to transport urease out of the cell and to shed it from its surface, (Evans, D. J. et al. "Urease-Associated Heat Shock Protein of *Helicobacter pylori*" Infect. Immun., vol. 60, 2125–2127 (1992), Ferrero, R. L. and Lee, A. "The Importance of Urease in Acid Protection for the Gastric-Colonizing Bacteria *Helicobacter pylori* and *Helicobacter felis* sp. nov." Microb. Ecol. Health Dis., vol. 4, 121–134 (1991)), thus urease may not represent an appropriate target for the development of a protective mucosal immune response. Indeed, mucosal immune protection is thought to be mainly mediated by secretory IgA, the agglutinating activity of which would be impaired when the recognized antigen can be shed by the target pathogen. Third, urease appears to be toxic for epithelial cells in culture, and has been suspected to play a role in mucus degradation and in peptic ulceration in vivo (Mégraud, F. et al., "Further Evidence of the Toxic Effect of Ammonia Produced by *Helicobacter pylori* Urease on Human Epithelial Cells," Infect. & Immun., vol. 60, 1858–63 (1992); Murakami, M. et al., "Gastric Ammonia has a Potent Ulcerogenic Action on the Rat Stomach," Gastroenterology 1993, vol. 105, 1710–15), thus its use as antigen may be toxic.

Nevertheless, we reasoned that this antigen could be a potentially efficient vaccine if:

first, we would deliver it orally at a sufficiently high dose to elicit a stronger immune response than the naturally occurring one second, the amount of antibodies produced would be high enough to bind all the urease, shed or not shed third, we would use subunits of urease or a molecular species that was non toxic.

Another aspect of the invention describes the use of antibodies directed against urease to prevent and to treat Helicobacter infection. European Patent Application No. 91310049.1, filed by Kunio Ando on *Oct.* 31, 1991, claiming priority on Japanese Patent Application No. 296609/90 filed Nov. 1, 1990, titled "A Method for Producing a new Medicine for Both Treating and Preventing Peptic Ulcer Diseases and Gastritis and Thus Formulated Medicines," describes the oral administration of polyclonal antibodies derived from bovine colostrum and bovine serum to patients with active chronic gastritis type B and to patients with duodenal ulcer. The Ando application describes the use of an antibody preparation directed against many antigens, including *Helicobacter pylori*, and does not disclose the use of an antibody directed against urease to treat or prevent *Helicobacter pylori* infection. The use of antibodies to treat gastric disease in gnotobiotic piglets was described in U.S. Pat. Nos. 5,258,178 and 5,260,057, issued to Cordle and Schaller and titled "Method and Product for the Treatment of Gastric Disease." The Cordle and Schaller patents describe the use of an antibody preparation that does not solely contain antibodies directed against *Helicobacter pylori*, and does not disclose the use of an antibody directed against urease to treat or prevent *Helicobacter pylori* infection. Nagata et al. describe the preparation of a monoclonal antibody directed against *Helicobacter pylori* that inhibits urease activity. (Nagata, K., et al., "Monoclonal Antibodies Against the Native Urease of *Helicobacter pylori*: Synergistic Inhibition of Urease Activity by Monoclonal Antibody Combinations," Infect. and Immun., Vol. 60,4826 (1992)). Nagata et al. do not describe the use of monoclonal antibodies directed against urease to prevent or to treat *Helicobacter pylori* infection.

Very few examples of therapeutic vaccines are available in the literature. Most of them are related to parenteral immunizations aimed to stimulate the host's immune system against malignant tumors, to modulate the immune system in autoimmune diseases such as rheumatoid arthritis or as desensitization in allergy states. Therapeutic vaccination procedures against different infections were also performed, most of them via a parenteral route of immunization. They included immunizations against leprosy in humans (Zaheer S A et al. "Combined Multidrug and *Mycobacterium w* Vaccine Therapy in Patients with Multibacillary Leprosy" J. Infect Dis., vol. 167, 401–410 (1993), Mukherjee A. et al., "Histopathological Monitoring of an Immunotherapeutic Trial with *Mycobacterium w*." Int. J Lepr. Other Mycobact. Dis., vol. 60, 28–35 (1992)), in complementation of antibiotic therapy, vaccination against *Phythiosis insidiori*, a mycological infection, in horses (Mendoza L, et al., "Evaluation of Two Vaccines for the Treatment of *Pythiosis insidiosi* in Horses" Mycopathologia, vol. 119, 89–95 (1992)), an uncontrolled study on the use of an autovaccine in chronic osteomyelitis (Sologub VV. "Experience in Using an Autovaccine in Treating Patients with Chronic Osteomyelitis" Vrach, Delo, 122–125 (1992)) and systemic immunization against Campylobacter fetus infection of female cattle (Schurig, G.G.D., et al., "Bovine Venereal Vibriosis: Cure of Genital Infection in Females by Systemic Immunization," Infect. & Immun., Vol. 11, 245–51 (1975)). To date, only one oral immunotherapy study aimed at stimulating the mucosal immune system in order to treat (and to prevent recurrence of) a mucosal infection has been performed, for urinary tract infection (Schulman CC, et al. "Oral Immunotherapy of Recurrent Urinary Tract Infections: A Double-Blind Placebo-Controlled Multicenter Study" J Urol., vol. 150, 917–921 (1993)). In that study, Schulman et al. used a lysate of selected *E. coli* strains, together with an concomitant treatment of antibiotics, chemotherapeutics or urinary tract disinfectants to treat the acute infection at entry in the study. Therefore, no study has demonstrated so far the effectiveness of a therapeutic vaccine, used as a monotherapy, administered to the mucosal immune system, against a bacterial disease.

The novelty of a therapeutic vaccine against Helicobacter infection also comes from the observation that *H. pylori* persists as a chronic infection in the gastric cavity for years, despite inducing a vigorous local and systemic immune response. This observation was conceptually already an obstacle to the development of a prophylactic vaccine against Helicobacter infection, but was even more an obstacle to the development of a therapeutic immunization.

In summary, there remains a need for effective treatment and prevention of *Helicobacter pylori*-induced gastric infection in humans. Recent data suggested the possibility to generate a vaccine against this infection, but have not provided a clear identification of defined antigen(s), common to all strains of *Helicobacter pylori*, that could be incorporated into a safe and effective vaccine.

In this invention, we have identified the urease antigen of *Helicobacter pylori* as a candidate vaccine and demonstrated its efficacy in an animal model. We have also demonstrated the use of the *Helicobacter pylori* urease antigen for the treatment and eradication of Helicobacter infection. We have further demonstrated that the B subunit of urease alone (ure B) is effective as a vaccine useful for the prevention of and treatment of Helicobacter infection. These results were unexpected in the light of the natural history of Helicobacter infections.

SUMMARY OF THE INVENTION

We have determined that it is useful to immunize animals with Helicobacter urease peptides for both prophylactic and therapeutic treatment. Immunization of animals with Helicobacter urease peptides prevents infection by Helicobacter and eradicates infection in previously infected animals. This method, and the vaccine compositions, are useful for the prevention and treatment of gastroduodenal disease associated with Helicobacter infection.

We have discovered that immunity can be induced in mammals susceptible to gastrointestinal Helicobacter infection by exploiting urease epitopes displayed on or about the surface of Helicobacter organisms and using them as a vaccine target. The immunity can be induced by immunization with native urease, but can also be induced with recombinant urease subunit, produced as an enzymatically inactive, therefore non-toxic form. The invention provides a method of inducing immunity to Helicobacter infection by administering to a mucosal surface of a mammal a polyaminoacid preparation, i.e. a mixture of peptides and/or proteins, together with an appropriate adjuvant. This polyaminoacid preparation presents a plurality of epitopes characteristic of and exhibited by a urease enzyme endogenous to the infecting Helicobacter organism. The administration of the polyaminoacid preparation may be performed by the oral route.

The active ingredient of the preparation may comprise natural or biosynthetic epitopes and may take various forms. A non exhaustive list of possible preparations includes purified, naturally occurring or recombinantly produced urease preparations of bacterial or other origin, digests of urease, fusion proteins comprising urease epitopes, truncated forms of urease enzyme, or peptides homologous with the amino acid sequence of urease. Since development of immunity depends on induction of humoral and/or cellular immune responses which bind to the infecting Helicobacter organism, preferred preparations are those which most closely duplicate the epitopes of the urease endogenous to the infecting organism. For example, preparations displaying the epitopes of urease of *Helicobacter pylori* are preferred for administration in humans susceptible to *Helicobacter pylori*, and preparations displaying the epitopes of urease of *H. felis* are preferred for the administration in humans susceptible to *H. felis*. However, in accordance with an important aspect of the invention, it has been discovered that urease from a heterologous species may be used. For example, we have shown that *H. felis* infection in mice can be prevented by administration of urease from *Helicobacter pylori*. Thus, *H. pylori* urease can be used to protect against *H. pylori* as well as *H. felis*. *H. felis* is an occasional cause of human infection and disease. (Wegman, W. et al., Schweig. Med. Wochenschr. vol. 121, 245–54 (1991)).

According to a first embodiment of the present invention, a method is provided of eliciting in a mammalian host a protective immune response to Helicobacter infection. According to a second embodiment of the present invention, a method is provided of treating a mammalian host that is infected with Helicobacter.

Thus, in a first aspect, the present invention provides a method of eliciting in a mammalian host a protective immune response to Helicobacter infection. The method comprises the step of administering to a mucosal surface of the mammal, including humans, an immunologically effective amount of a urease antigen, preferably *Helicobacter pylori* urease, capable of eliciting such a protective immune response. The term "comprising" is used herein as it is recognized in the art.

According to one aspect of the invention, there is provided a method of eliciting in a mammalian host a protective immune response to Helicobacter infection wherein an immunologically effective amount of a urease antigen capable of eliciting such a protective immune response, preferably *Helicobacter pylori* urease or *Helicobacter pylori* urease B subunit, is administered to a mucosal surface of the host.

In a second aspect, the present invention provides a method of eliciting in a mammalian host a protective immune response to Helicobacter infection. The method comprises the step of administering to a mucosal surface of the mammal, including humans, an immunologically effective amount of recombinant, enzymatically inactive, urease B subunit as antigen, preferably recombinant *Helicobacter pylori* urease B subunit, capable of eliciting such a protective immune response.

The invention also includes within its scope the treatment or prophylaxis of mammals, including humans, for Helicobacter infection, wherein an immunologically effective amount of a urease, or its subunits, capable of eliciting a protective immune response to Helicobacter infection, is administered to a mucosal surface of a patient. Preferably, the urease is *Helicobacter pylori* urease or *Helicobacter pylori* urease B subunit, and the urease is preferably administered in particulate form in association with a hydroxylated calcium phosphate, for example hydroxyapatite. Moreover, it is preferred to administer the *Helicobacter pylori* urease in association with a mucosal adjuvant, the B subunit of cholera toxin, muramyl dipeptide or other such adjuvants.

According to another aspect of the present invention, there is provided a vaccine composition suitable for prevention of Helicobacter infection, comprising an effective amount of a urease antigen, preferably *Helicobacter pylori* urease or *Helicobacter pylori* urease B subunit, or recombinant *Helicobacter pylori* urease subunits, capable of eliciting in a host a protective immune response to Helicobacter infection, in association with a pharmaceutically acceptable carrier or diluent. Suitable carriers and diluents will be recognized by those skilled in the art and can be found in, for example Remington's Pharmaceutical Sciences (18th ed., 1990).

The vaccines of the invention are administered in amounts readily determined by persons of ordinary skill in this art. Thus, for adults a suitable dosage will be in the range of 10 μg to 100 milligrams, for example 50 μg to 50 mg. A suitable dosage for adults will also be in the range of 5 μg to 500 mg. Similar dosage ranges will be applicable for children. Carrier systems in humans may include enteric release capsules protecting the antigen from the acidic environment of the stomach, and including urease antigen in a insoluble form as fusion proteins. The vaccine can be administered as a primary prophylactic agent in adults or in children, as a secondary prevention, after successful eradication of *Helicobacter pylori* in an infected host, or as a therapeutic agent in the aim to induce an immune response in the host susceptible to contribute to the eradication of *Helicobacter pylori*.

As noted above, a suitable mucosal adjuvant is cholera toxin. Others which may be used are non-toxic derivatives of cholera toxin, including its B subunit, and/or conjugates or genetically engineered fusions of the urease antigen plus cholera toxin or its B subunit. Other suitable delivery methods include biodegradable microcapsules or immunostimulating complexes (ISCOMs) or liposomes, genetically engineered attenuated live vectors such as viruses or bacteria, and recombinant (chimeric) virus-like particles, e.g. bluetongue. The amount of mucosal adjuvant employed depends on the type of mucosal adjuvant used. For example, when the mucosal adjuvant is cholera toxin, it is suitably used in an amount of 5 μg to 50 μg, for example 10 μg to 35 μg. When used in the form of microcapsules, the amount used will depend on the amount employed in the matrix of the microcapsules to achieve the desired dosage. The determination of this amount is within the skill of a person of ordinary skill in this art.

Suitable carriers for the vaccines of the invention are enteric coated capsules and polylactide-glycolide microspheres. Suitable diluents are 0.2N $NaHCO_3$ and/or saline.

Particulate hydroxylated calcium phosphate (HCP) is especially useful as a carrier for the *Helicobacter pylori* urease to be applied to mucosal surfaces. It is believed that the *Helicobacter pylori* urease-hydroxylated calcium phosphate conjugate is transported across epithelium where it raises a poly Ig immune response. Preferably, the hydroxylated calcium phosphate is in the form of microparticles suitable for transport across the epithelium, particularly by cells specialized for this purpose (M cells). A preferred form of hydroxylated calcium phosphate is hydroxyapatite, a commercially available crystalline hydroxylated calcium phosphate $Ca_{10}(PO_4)_6(OH)_2$. Commercially available hydroxyapatite generally consists of slab-like crystals that are chemically and physically analogous to inorganic hydroxyapatite in normal bone tissue. Ingestion of hydroxyapatite should therefore be safe, as evidenced by the existence of nutritional calcium/phosphorus supplements derived from ground bone, which are designed to be ingested. Commercially-high resolution hydroxyapatite (from CalBiochem) consists of crystals varying widely in size. Crystals over 1 μm in length are unlikely to be taken up by M cells. Therefore, for use in the invention, commercial hydroxyapatite crystals are broken into small, relatively uniform crystalline fragments such as by sonication. Preferably, a substantial proportion of the hydroxyapatite is present as fragments of about 0.01–1.0 μm. Fragmentation may be measured either by electron microscopy or light scattering, using standard techniques.

Preferred modes of administration of the *Helicobacter pylori* urease antigen are orally, nasally, rectally or ocularly. Oral administration can provide delivery to other G.I. (gastrointestinal) mucosa including the intestinal mucosa.

The vaccines of the present invention may be administered to a mucosal surface in the form of an aerosol, suspension, capsule and/or suppository. The method of administration will be readily apparent to a person of ordinary skill in this art and can be found in, for example, Remington's Pharmaceutical Sciences (18 ed., 1990).

According to a further aspect of the present invention, there is provided a method of imparting to a mammalian host passive protection to Helicobacter infection, comprising administering to a mucosal surface of the host an immunologically effective amount of a urease specific antibody produced in a host immunized with a urease, preferably *Helicobacter pylori* urease or *Helicobacter pylori* urease B subunit, capable of eliciting a protective immune response to Helicobacter infection.

The present invention further includes the passive immunization of mammals, including humans, against Helicobacter infection. This is achieved by administering to a mucosal surface of the patient an effective amount of a urease specific antibody, preferably, an effective amount of a *Helicobacter pylori* urease specific IgA monoclonal antibody.

Since the urease of *Helicobacter pylori* is shown to represent the antigen involved in inducing protective immunity, a further aspect of the invention is the use of *Helicobacter pylori* urease as a diagnostic reagent to measure the immune response of persons who have received a vaccine based on urease or to determine whether an individual is immune or susceptible (and thus in need of vaccination). The present invention also includes the use of urease and urease-specific antibodies to construct assays and kits for diagnosis of Helicobacter immunity, assessment of Helicobacter susceptibility, and definition of immune responses to vaccines.

In a third aspect, the invention provides a method of treating gastroduodenal disease in a mammal. This method comprises the step of administering a therapeutically effective amount of a composition comprising Helicobacter urease peptides. The gastroduodenal diseases included within the scope of the invention include, but are not limited to, gastritis, peptic ulcer disease, including both gastric and duodenal ulcers, gastric cancer, chronic dyspepsia with severe erosive gastroduodenitis, refractory ulcer dyspepsia, intestinal metaplasia, low grade MALT lymphoma, Helicobacter infection, Helicobacter pylori infection and *Helicobacter felis* infection. The term "urease peptides" refers to, but is not limited to, any urease or subunit or urease, either naturally occurring or obtained by recombinant DNA techniques, as well as a digested fragment or peptide thereof, fusion proteins comprising the whole urease, subunits, or fragments thereof, or truncated urease constructs. Also included within the term "urease peptides," are proteins or peptides that display epitopes sufficiently homologous to epitopes displayed by Helicobacter urease such that antibodies that recognize epitopes displayed by Helicobacter urease will recognize epitopes displayed by said peptides or proteins.

In a more particular related aspect, the invention provides a method of treating gastroduodenal disease caused by Helicobacter infection. The Helicobacter infection may be, but is not limited to, *Helicobacter pylori* or *H. felis* infection.

More particularly, the invention provides a method of treating gastroduodenal disease caused by Helicobacter infection whereby the composition comprising Helicobacter urease peptides is administered to a mucosal surface. Without limiting the type of mucosal surface used for administration, the mucosal surface may be oral, nasal, rectal, or ocular.

The invention can also feature the administration of a composition comprising Helicobacter urease peptides in association with a mucosal adjuvant. The mucosal adjuvant may be selected from, but is not limited to, cholera toxin, procholeragenoid, cholera toxin B subunit, fungal polysaccharides including, but not limited to, schizophyllan, muramyl dipeptide, muramyl dipeptide derivatives, phorbol esters, microspheres, non-*Helicobacter pylori* bacterial lysates, labile toxin of *Escherichia coli*, block polymers, saponins, and ISCOMs. Other mucosal adjuvants will be recognized to those in the art and can be found in, for example, Azuma, I., "Synthetic Immunoadjuvants: Application to Non-Specific Host Stimulation and Potentiation of Vaccine Immunogenicity" Vaccine, vol. 10, 1000 (1992); Pockley, A. G. & Montgomery, P. C., "In vivo Adjuvant Effect of Interleukins 5 and 6 on Rat Tear IgA Antibody Responses" Immunology, vol. 73, 19–23 (1991); Adam, A. & Lederer, E. "Muramyl peptides as Immunomodulators" *ISI ATLAS OF SCIENCE* 205 (1988); Clements, J. D., et al. "Adjuvant Activity of *Escherichia coli* Heat-labile Enterotoxin and Effect on the Induction of Oral Tolerance in Mice to Unrelated Protein Antigens" Vaccine, vol. 6, 269 (1988); Ben Ahmeida, E. T. S., et al. "Immunopotentiation of Local and Systemic Humoral Immune Responses by ISCOMs, Liposomes and FCA: Role in Protection Against Influenza A in Mice" Vaccine, vol. 11, 1302 (1993); and Gupta, R. K. et al. "Adjuvants—A Balance Between Toxicity and Adjuvanticity" Vaccine, vol. 11, 290–308 (1993).

The mucosal adjuvant may also be genetically or chemically linked to the urease peptides. Examples of this type of fusion peptide are known to those skilled in the art and can also be found in Czerkinsky et al., "Oral Administration of a Streptococcal Antigen Coupled to Cholera Toxin B Subunit Evokes Strong Antibody Responses in Salivary Glands and Extramucosal Tissues" Infect. Immun., vol. 57, 1072–77 (1989); Nashar et al., "Current Progress in the Development of the B Subunits of Cholera Toxin and *Escherichia Coli* Heat-Labile Enterotoxin as Carriers for the Oral Delivery of Heterologous Antigens and Epitopes" Vaccine, vol. 11, 235–40 (1993); and Dertzbaugh and Elson, "Comparative Effectivess of the Cholera Toxin B Subunit and Alkaline Phosphatase as Carriers for Oral Vaccines," Infect. Immun., vol. 61, 48–55 (1993). For example, the urease B subunit could be expressed as a chimeric protein that is genetically linked to the cholera toxin B subunit through the use of a DNA expression vector containing the ure B nucleotide sequence linked to the cholera toxin B subunit nucleotide sequence.

In another related aspect, the method involves the administration of a composition comprising Helicobacter urease peptides where such composition is delivered in particulate form. The composition may be delivered in particulate form through association with a carrier. The carrier may be a hydroxylated calcium phosphate, for example, hydroxyapatite. The term "hydroxyapatite" refers to, but is not limited to, its meaning as is recognized by those skilled in the art to mean a tribasic calcium phosphate, also known as hydroxylated calcium phosphate or calcium hydroxide phosphate. This is only an example, and is not meant to be limiting as to the type of carrier that may be used.

In another related aspect, the administered dosage of the composition comprising Helicobacter urease peptides may range from 100 μg to 1g, for example, 0.14 mg to 14.4 mg per kg of body weight. Those of skill in the art will recognize that the optimal dose may be more or less depending upon the patient's body weight, disease, the route of administration, and other factors. The dosage level is readily determinable by standard methods. The number of doses will depend upon the disease, the formulation, and efficacy data from clinical trials. For example, the dosage may be administered over 3 to 8 doses for a primary immunization schedule over 1 month. This course of treatment is an example and is not meant to be limiting.

In one related aspect, the method involves the administration of a composition comprising Helicobacter urease peptides wherein the composition is administered in association with a microsphere carrier. Such microsphere carrier may be, for example, but is not limited to, a polylactide-coglycode biodegradable microsphere carrier.

In another related aspect, the method involves the administration of a composition comprising the Helicobacter urease peptides wherein such composition comprises a recombinant live vector which expresses a Helicobacter urease peptide. Those skilled in the art will recognize that such live vector may be, for example, a bacterial or a viral vector. For example, without any limitation, the live vector may be selected from the group consisting of *Salmonella typhimurium*, *Salmonella typhi*, Shigella, Bacillus, Lactobacillus, BCG, *Escherichia coli*, *Vibrio cholerae*, Campylobacter, yeast, Herpes virus, Adenovirus, Poliovirus, Vaccinia, and Avipox. In addition, a carrier system which expresses a Helicobacter urease peptide, such as Bluetongue virus-like particles, Rotavirus-like particles, and Ty particles, may be used to deliver the urease peptide. In a preferred aspect, the live vector or the carrier system may be administered to a mucosal surface.

A preferred embodiment of the present invention comprises a method of treating a human infected with *Helicobacter pylori*, comprising orally administering a therapeutically effective amount of a composition comprising the ure B subunit of *Helicobacter pylori* urease, in association with a mucosal adjuvant selected from the group consisting of cholera toxin, procholeragenoid, cholera toxin B subunit, fungal polysaccharides, including schizophyllan, muramyl dipeptide, muramyl dipeptide derivatives, phorbol esters, liposomes, microspheres, non-*Helicobacter pylori* bacterial lysates, labile toxin of *Escherichia coli*, block polymers, saponins, and ISCOMS, the composition being administered in a particulate form in association with hydroxyapatite. The composition may also be administered with concurrent oral administration of a chewable 1.0 g $NaHCO_3$ tablet. For the purposes of this invention, the term "in association with" includes any type of association, including but not limited to, a chemical or genetic association, such as that present in a fusion protein.

In a fourth aspect, the invention provides a method of treating gastroduodenal disease in a mammal, comprising administering a therapeutically effective amount of a composition comprising an antibody that recognizes Helicobacter urease. The gastroduodenal diseases included within the scope of the invention are referenced above. These methods use the above-referenced composition comprising Helicobacter urease peptides to elicit an antibody response in a mammal. The antibodies produced by the immunized mammal are isolated and administered to the subject mammal. The preparation of antibodies that recognize a given antigen, such as the above-referenced composition, is known to those skilled in the art. For example, polyclonal and monoclonal antibodies can be prepared following the disclosure in Harlow, E. & Lane, D., *Antibodies: A Laboratory Manual* (1988).

In a more particular related aspect, the administered antibody is a monoclonal antibody. The preparation of monoclonal antibodies is known to those skilled in the art.

More particularly, the administered antibody is an IgA antibody, either a polyclonal or monoclonal IgA antibody. The preparation of monoclonal IgA antibodies is known to those skilled in the art and may be found in, for example, Winner, L., et al., "New Model for Analysis of Mucosal Immunity: Intestinal Secretion of Specific Monoclonal Immunoglobulin A from Hybridoma Tumors Protects Against *Vibrio Cholerae* Infection" Infect. and Immun., vol. 59, 977–982 (1991); and Weltzin, R., et al., "Binding and Transepithelial Transport of Immunoglobulins by Intestinal M Cells: Demonstration Using Monoclonal IgA Antibodies Against Enteric Viral Proteins" J. Cell Biol., vol. 108, 1673–1685 (1989).

The term "antibody" as used for the purposes of this invention includes, but is not limited to, polyclonal antibodies, monoclonal antibodies, and anti-idiotypic antibodies. The antibodies may be naturally derived from any animal, synthesized in bacteria or another non-animal source, chemically synthesized, or genetically synthesized.

In a preferred aspect of the invention, a method is provided of treating a human infected with *Helicobacter pylori*, comprising administering a therapeutically effective amount of a composition comprising an IgA monoclonal antibody that recognizes the ure B subunit of *Helicobacter pylori* urease.

In a fifth aspect, the invention provides a composition useful in the therapeutic treatment of gastroduodenal disease, comprising Helicobacter urease peptides. The gastroduodenal diseases included within the scope of the invention, as well as the Helicobacter urease peptides and mucosal adjuvants included within the scope of the invention, are referenced above.

In a related aspect, the composition comprises Helicobacter urease peptides and a mucosal adjuvant.

In another related aspect, the composition is in particulate form. The composition may exist in particulate form through association with a carrier. The carrier may be, for example, hydroxyapatite, as referenced above. This is only an example, and is not meant to be limiting as to the type of carrier that may be used.

More particularly, the composition is present in particulate form, in a liquid suspension.

In a related aspect, the composition comprises Helicobacter urease peptides in association with a microsphere carrier. Such microsphere carrier may be, for example, but is not limited to, a polylactide-coglycolide biodegradable microsphere. The urease peptides may encapsulated in the biodegradable microspheres. Polylactide-coglycolide microspheres slowly hydrolyze in the presence of water and becomes water-soluble, thus delivering the peptides that are incorporated in the microsphere.

In another related aspect, the composition comprises Helicobacter urease peptides wherein the composition comprises a recombinant live vector which expresses a Helicobacter urease peptide. Those skilled in the art will recognize that such live vector may be, for example, a bacterial or a viral vector. for example, without any limitation, the live vector may be selected from the group consisting of *Salmonella typhimurium, Salmonella typhi*, Shigella, Bacillus, Lactobacillus, BCG, *Escherichia coli, Vibrio cholerae*, Campylobacter, yeast, Herpes virus, Adenovirus, Poliovirus, Vaccinia, and Avipox. In addition, a carrier system which expresses a Helicobacter urease peptide, such as Bluetongue virus-like particles, Rotavirus-like particles, and Ty particles, may be used to deliver the urease peptide. In a preferred embodiment, a composition is provided that is useful in the therapeutic treatment of *Helicobacter pylori* infection of a human, comprising the ure B subunit of *Helicobacter pylori* urease, a mucosal adjuvant selected from a group consisting of cholera toxin, procholeragenoid, cholera toxin B subunit, fungal polysaccharides, including schizophyllan, muramyl dipeptide, muramyl dipeptide derivatives, phorbol esters, liposomes, microspheres, non-*Helicobacter pylori* bacterial lysates, labile toxin of *Escherichia coli*, block polymers, saponins, and ISCOMs, and further comprising hydroxyapatite, wherein the composition is in a particulate form in a liquid suspension. The term "in association with" is defined as referenced above.

In a sixth aspect, a composition is provided that is useful in the therapeutic treatment of gastroduodenal disease, comprising an antibody that recognizes Helicobacter urease. The gastroduodenal disease included within the scope of the invention, as well as the antibodies included within the scope of the invention, are referenced above.

In a preferred embodiment of the invention, a composition is provided that is useful in the therapeutic treatment of gastroduodenal disease, comprising an IgA monoclonal antibody that recognizes the ure B subunit of *Helicobacter pylori* urease. While not being bound by any theory, the present inventors believe that administration of the urease antigen, or B subunit thereof, to a mucosal surface stimulates the common mucosal immune system and perhaps local sites in the gastric mucosa inducing an immune response, including the appearance of *Helicobacter pylori* specific IgA antibodies in the gastric secretions, which prevent Helicobacter infection. Because of this belief, the terms "immunization" and "vaccine" are used herein by their common meanings as recognized by those skilled in the art and also to indicate methods and compositions used for the treatment of Helicobacter infection, without limitation to these meanings, and without being bound to any theory regarding the mechanism of treatment.

Since it is a routine matter to conduct pre-clinical trials of candidate vaccines for human use in animal models, it is believed that the methodology of the present invention is effective in humans, especially in the prevention and treatment of peptic ulcers, gastritis, gastric malignancies and other conditions arising as a result of the presence of *Helicobacter pylori* and/or *H. fells*.

Based on the dosage and course of treatment that successfully eradicated infection in the mouse model, a preferred range of dosage would be 100 μg to 10 g of Helicobacter urease peptides. Those skilled in the art will recognize the appropriate dosage level to test from research reported for other oral vaccines such as, for example, the research performed with *Escherichia coli* lysate (6 mg dose daily up to a total of 540 mg) and with an enterotoxigenic *E. coli* purified antigen (4 doses of 1 mg). (Schulman et al, "Oral Immunotherapy of Recurrent Urinary Tract Infections: A Double-Blind Placebo-Controlled Multicenter Study," J. Urol., vol. 150, 917–921 (1993); Boedeker et al., "Safety, Immunogenicity and Efficacy in Human Volunteers of Biodegradable, Biocompatible Microspheres Containing Colonization Factor Antigen/II (CFA/II) as an Enteral Vaccine Against Enterotoxigenic *E. coli* (ETEC)" American Gastroenterological Assoc., vol. 999, A-222 (1993)). Without intending any limitation as to the course of treatment, the treatment could be administered over 3 to 8 doses for a primary immunization schedule over 1 month. (Boedeker, American Gastroenterological Assoc., vol. 888, A-222 (1993)).

A recommended method of immunization is administration of the Helicobacter urease peptide composition in the form of a liquid alone or suspension containing $Na_2HCO_3$ or similar material to temporarily neutralize gastric acid. The neutralizing material may also be delivered separately at the time the peptide composition is administered, such as in the form of a chewable $Na_2HCO_3$ tablet. Alternatively, the composition can be administered in the form of enteric-coated capsules. These methods will likely avoid the problem of degradation of the urease composition during its passage in the upper gastrointestinal tract. These methods are reviewed in, for example, Levine & Norlega, "Vaccines to Prevent Enteric Infections," Ballieres Clin. Gastro., vol. 7, 501–517 (1993).

Although a high dose of cholera toxin is not preferred as a mucosal adjuvant for human use, other mucosal adjuvants recognized by those skilled in the art, and as referenced above, will be useful for treatment of humans.

It will be readily apparent to one skilled in the art that varying substitutions and modifications may be made to the invention disclosed herein without departing from the scope and spirit of the invention.

BRIEF DESCRIPTION OF THE DRAWINGS

The invention will now be further described with reference to the accompanying drawings, in which

FIG. 1 is a graphic representation of the results from Table 1 of the tests for antibodies in serum (IgG) and intestinal secretion (IgA) in mice that were not protected after immunization with urease.

FIG. 2 is a graphic representation of the results from Table 1 of tests for antibodies in serum (IgG) and intestinal secretion (IgA) in mice that were protected after immunization with urease.

FIG. 3 is a graphic representation of the results from Table 1 of tests for antibodies in serum (IgG) and intestinal secretion (IgA) in mice that were not protected after immunization with *Helicobacter pylori* sonicate.

FIG. 4 is a graphic representation of the results from Table 1 of tests for antibodies in serum (IgG) and intestinal secretion (IgA) in mice that were protected after immunization with *Helicobacter pylori* sonicate.

FIG. 5 is a graphic representation of the results set out in Table 2 comparing the level of protection obtained with *Helicobacter pylori* urease as compared to that obtained with *Helicobacter pylori* sonicate and with cholera toxin.

FIG. 6 is a graphic representation of the results set out in Tables 5 and 6 which measures urease activity in mice that were challenged after oral immunization with recombinant urease A and B subunits.

FIG. 7 is a graphic representation of the results set out in Table 8 which measures gastric tissue urease activity as a reflection of Helicobacter infection in mice that were subsequently treated with the *Helicobacter pylori* ure B subunit, cholera toxin and hydroxyapatite only (sham immunized), or untreated.

FIG. 8 is a graphic representation of the results set out in Table 9 which measures gastric tissue urease activity as a reflection of Helicobacter infection in mice that were subsequently treated with the *Helicobacter pylori* ure B subunit, or cholera toxin and hydroxyapatite only (sham immunized). For FIG. 8A, the mice were sacrificed and urease assays performed 2.5 weeks after the last immunization. For FIG. 8B, the mice were sacrificed and urease assays performed 8 weeks after the last immunization.

DETAILED DESCRIPTION OF THE INVENTION

Figure 1:
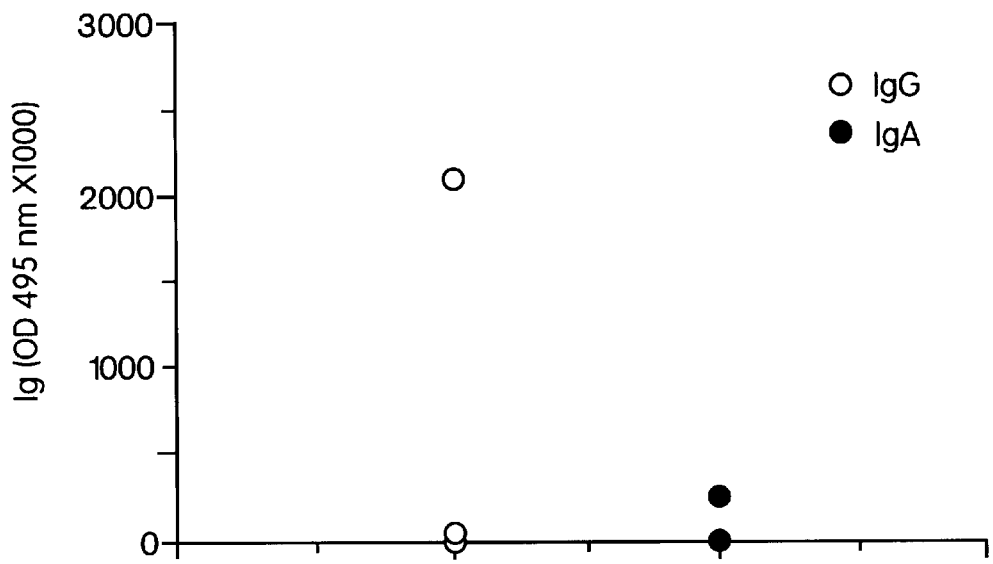
FIGS. 1 through 8 are graphical representations of the results set forth in Tables 1 through 9.

The present inventors have discovered that oral administration to mice of polyaminoacid preparations exhibiting the epitopes of *Helicobacter pylori* urease gives rise to a protective immunological response against *H. felis* in mice, an animal model of generally-accepted value for the study of the immune response to Helicobacter infection (Lee, A. et al. "A Small Animal Model of Human *Helicobacter pylori* Active Chronic Gastritis" Gastroenterology, vol. 99, 1315–1323 (1990)), and a recognized pathogen causing gastritis in humans (Wegman, W. et al., Schweig. Med. Wochenschr., vol. 121, 245–54 (1991)). The effect of the protective immune response is that immunized animals, when challenged with pathogen, have a greatly reduced incidence of infection, in comparison to non-immunized animals. Furthermore, the inventors have discovered that oral immunization in mice using *Helicobacter pylori* urease B subunit, produced as an enzymatically-inactive recombinant protein, gives rise to a protective immunological response in mice against *H. felis*. The effect of the protective immune response is that immunized animals, when challenged with pathogen, have also a greatly reduced incidence of infection, in comparison to non-immunized animals which do become infected.

The present inventors have discovered that oral administration of Helicobacter urease peptides to mice infected with *H. felis* results in the clearance of the infection. This result indicates that the oral administration of Helicobacter urease peptides is an effective therapy for the treatment of Helicobacter infection in mammals. The oral administration of *Helicobacter pylori* urease B subunit, produced as an enzymatically-inactive recombinant protein significantly decreases the level of *H. felis* infection in infected mice, in comparison to control infected mice.

The following examples are offered by way of illustration and are not intended to limit the invention in any manner.

A. Bacterial Cultures and Urease Purification

The strain of *Helicobacter pylori* used in the study originates from a patient with a duodenal ulcer, and has been subcultured on BHI agarose plates to homogeneity. *Helicobacter pylori* is cultured in a suitable medium, typically, BHI (Brain-Heart Infusion) medium, containing 0.25% yeast extract and 10% fetal calf serum and supplemented with 0.4% Campylobacter selective complement (Skirrow supplement; Oxoid 69). The bacteria are incubated under microaerophilic conditions at 37° C. in bottles that are sealed and shaken at 37° C. for 2 to 3 days to produce a liquid culture. A culture may also be prepared in agarose plates consisting of BHI with 0.250% of yeast extract and 5% of sheep blood under microaerophilic conditions at 37° C. for 3 days. The quantity of bacteria is determined by optical density of the BHI solution at 660 nm, with one optical density unit corresponding to $10^8$ bacteria. Cultures on agarose plates are first resuspended in 154 mM NaCl.

One currently preferred source of polyaminoacid displaying urease epitopes is purified urease, e.g., *Helicobacter pylori* urease obtained by following the general method of Dunn et al. J. Biol. Chem. 265, 9464–9469, modified as described below. Following culturing, the *Helicobacter pylori* is harvested in water, spun vortexed and spun again to produce a supernatant. The solution containing the urease activity of *Helicobacter pylori* (assessed by rapid urease test, see below) is then chromatographed on a CL-6B sizing column and the fractions which present a strong urease activity are pooled and dialysed over-night and again chromatographed on an anion exchanger gel. The fractions are eluted in increasing NaCl buffer and the collected fractions with a strong urease activity are individually submitted to a SDS gel followed by Coomassie staining. Two distinct bands corresponding to a molecular weight of about 63 and about 28 kDa are identified as urease. The fractions containing urease are pooled to give purified *Helicobacter pylori* urease having a purity in the region of 95% to 99%.

B. Oral Immunization with Urease Purified from *Helicobacter pylori*

While it is preferred to employ purified *Helicobacter pylori* urease obtained as described above as the antigenic material, it will be understood that it is also possible to use, as the antigenic material, any urease or subunit of urease, either naturally occurring or obtained by recombinant DNA techniques, as well as digested fragment thereof, fusion proteins comprising the fragments or the whole urease, truncated urease constructs, or other peptide or protein preparations exhibiting urease epitopes which are capable of eliciting a protective immune response to Helicobacter infection (See below). Thus, it is possible to employ a urease having a substantial homology with respect to *Helicobacter pylori* urease and which is effective in raising a cross-protective immune response to Helicobacter. An example of such a urease is jack bean urease, which possesses about 70% homology with *Helicobacter pylori* urease. Although it was once thought that jack bean urease would be an effective antigen to prevent infection by Helicobacter, this is no longer believed to be the case. (See Chen, M. et al. "Failure of Immunization Against Helicobacter Using Jack Bean Urease," Acta Gastroenterol. Belg., Vol. 56, 94 (1993)). The invention is therefore not limited to the use of intact urease, and covers the use of any polyaminoacid preparation which displays urease epitopes sufficiently homologous to *Helicobacter pylori* urease to generate a protective immunological response in a host to Helicobacter infection. A suitable urease must have sufficient homology to *H. pylori* urease to elicit a protective immune response against Helicobacter infection. Typically, a urease having a homology of greater than 70%, for example, 80–90% homology, with respect to *Helicobacter pylori* urease, may be employed as the urease antigen in the invention.

A non-limiting list of sources of potentially useful urease preparations includes endogenous urease enzymes of the different Helicobacter species, urease from other bacteria such as *Klebsiella pneumoniae* or *Proteus mirabilis*, and, by analogy, any other urease which the condition that these ureases share cross-reactive epitopes with *Helicobacter pylori* urease. The urease genes of all the organisms mentioned above represent a potential tool for expressing recombinant urease products as a whole protein or as a part thereof.

A non-limiting list of potentially useful urease preparations includes peptides generated from purified urease (the sources are mentioned above), using physical and/or chemical cleavage procedures (i.e. CnBr) and/or proteolytic cleavage (using proteases e.g. V8-protease, trypsin or others); or peptides synthesized chemically and retaining crossreactive epitopes with urease.

Other sources of potentially useful epitopes include epitopes identified by their crossreactivity with urease, as the result of screening with anti-urease antibodies. These peptides can be naturally occurring peptides or peptides resulting from chemical synthesis. Furthermore such peptides can result from the expression of recombinant random oligonucleotides.

Another source of potentially useful epitopes includes epitopes similar to urease as a result of the generation of anti-idiotypic antibodies to urease. Such anti-idiotypic antibodies, generated in any immunocompetent host, are obtained by immunization of this host with anti-urease antibodies, with the goal of generating antibodies directed against anti-urease antibodies, which share structural homologies with urease.

The discussion herein focuses on the use of urease naturally produced by *Helicobacter pylori* (section B). However, it will be appreciated that the urease or subunits or constructs thereof mentioned above, capable of eliciting the desired protective immune response, may be produced by recombinant DNA techniques well known in the art. The efficacy of particular preparations may be determined by routine administration using animal models, oral administration of the candidate vaccine, and challenge with pathogen using a protocol substantially similar or identical to the procedure described below.

It will be recognized by those skilled in the art that other methods may be used to administer the Helicobacter urease peptides. For example, the urease peptides may be administered as part of a microsphere carrier formulation. Without limiting the type of microsphere carriers used, one example would be the administration of the urease peptides as part of a polylactide-coglycolide biodegradable microsphere carrier formulation.

Another method of administering the Helicobacter urease peptides would be to express the urease peptides in a recombinant form in a live vector, for example, a bacterial or a viral vector. To construct such a live vector, nucleotide sequences coding for urease peptides would be incorporated into the genetic material of a live vector. Such live vector would be administered to an individual for the purpose of preventing Helicobacter infection and also for the purpose of treating an individual already infected with Helicobacter. Those skilled in the art will recognize that examples of appropriate live vectors include *Salmonella typhimurium, Salmonella typhi*, Shigella, Bacillus, Lactobacillus, BCG, *Escherichia coli, Vibrio cholerae*, Campylobacter, yeast, Herpes virus, Adenovirus, Poliovirus, Vaccinia, and Avipox. In addition, a recombinant carrier system which expresses a Helicobacter urease peptide, such as Bluetongue virus-like particles, Rotavirus virus-like particles, or Ty particles, may be used to deliver the urease peptide. The aforementioned list is not meant to be limiting. Preferably, the live vector or the carrier system would be administered mucosally such that the recombinant urease peptides expressed by the live vector would be administered to a mucosal surfa ce.

Tables 1 and 2 below and FIGS. 1–5 describe the results obtained when mice were orally immunized with purified *Helicobacter pylori* urease. In this first experiment, administration of the *Helicobacter pylori* antigen was carried out by orally administering to the mice *Helicobacter pylori* urease purified as described in section A, and coupled to hydroxyapatite crystals, used as a carrier to enhance M cell binding and uptake. Cholera toxin (Sigma) was given as a mucosal adjuvant. In this experiment, groups of female SPF BALB/c six-week old mice were each orally immunized with 30 $\mu$g of purified *Helicobacter pylori* urease coupled to 1 mg of hydroxyapatite plus 10 $\mu$g of cholera toxin adjuvant at day 0, 7, 14 and 21. The mice were then challenged twice with $10^8$ *H. felis*, at day 28 and 30. For comparison purposes, similar female SPF BALB/c six-week old mice were orally immunized with whole *Helicobacter pylori* lysate (sonicate) and 10 $\mu$g cholera toxin at day 0, 7, 14 and 21. The mice were challenged at day 28 and 30 with *H. felis*. The

*Helicobacter pylori* sonicate was prepared by collecting *Helicobacter pylori* from cell cultures, pelleting by centrifugation and resuspending the pellet in 0.9% sodium chloride followed by sonication.

As a control, female SPF BALB/c six-week old mice were orally sham-immunized with 10 µg of cholera toxin and 1 mg of hydroxyapatite at day 0, 7, 14 and 21. The mice were then challenged at day 28 and 30 with *H. felis*. All mice were housed and immunized in parallel. All mice subject to the study were sacrificed on day 35.

C. Oral Immunization with Recombinant Urease Subunits of *Helicobacter pylori*

Genes encoding the structural A and B subunits of *Helicobacter pylori* urease were obtained by polymerase chain reaction (PCR) cloning according to standard procedures, based on previously published sequences. (Clayton, C. L. et al. S. "Nucleotide Sequence of Two Genes from *Helicobacter pylori* Encoding for Urease Subunits" Nucleic Acid Res., vol. 18, 362 (1990)). These genes were inserted in a vector (named pEV40) designed for high expression and easy purification of foreign genes in *E. coli*. Briefly, the foreign gene is inserted down-stream of a thermo-repressible promoter, and in frame of a sequence encoding for a repeat of six histidines. An ampR gene is present on this vector for selection of transformants. Under the appropriate temperature conditions, the recombinant protein obtained is supplemented by six histidines at the N-terminal, which allow for a one-step affinity purification on a nickel column. Both *Helicobacter pylori* recombinant urease A and B subunits were expressed separately in *E. coli*, and purified on a nickel column to >95% purity.

While it is preferred to employ recombinant *Helicobacter pylori* urease obtained as described above as the antigenic material, it will be understood that it is also possible to use, as the antigenic material, any urease or subunit of urease obtained by recombinant techniques (e.g. fusion protein) expressing antigenic sites of urease, which is capable of eliciting a protective immune response to Helicobacter infection. Thus, it is possible to employ in a construct a urease gene having a substantial homology with respect to *Helicobacter pylori* urease and which is effective in raising a cross-protective immune response to Helicobacter. Examples of such a urease is jack bean urease, which possesses about 70% homology with *Helicobacter pylori* urease, or *H. felis* urease, which possesses about 88% homology with *Helicobacter pylori* urease. The invention is therefore not limited to the use of *Helicobacter pylori* urease genes and their gene products, and covers the use of any recombinant urease, or the subunits thereof, which is sufficiently close antigenically to generate a protective immunological response in a host to Helicobacter infection. The invention includes within its scope the use of any urease or subunit of urease, either naturally occurring or obtained by recombinant DNA techniques, as well as a digested fragment or peptide thereof, fusion protein comprising the whole urease, subunit or fragment thereof, or truncated urease construct which is effective in reducing the level of Helicobacter infection in an infected mammal. Typically, a recombinant urease having a homology of 70–95% homology, for example, 80–90% homology, with respect to *Helicobacter pylori* urease, may be employed as the recombinant urease antigen in the invention.

The discussion herein focuses on the use of recombinant *Helicobacter pylori* urease A and B subunits produced by *E. coli* (section C). However, it will be appreciated that recombinant urease or subunits or constructs thereof mentioned above, capable of eliciting the desired protective immune response, may be produced using other recombinant DNA techniques and other eukaryotic or prokaryotic expression vectors well known in the art.

Tables 3, 4 and 5 below and FIG. 6 describe the results obtained when mice were orally immunized with recombinant *Helicobacter pylori* urease subunits produced in *E. coli*. In this experiment, administration of the *Helicobacter pylori* antigen was carried out by orally administering to the mice recombinant *Helicobacter pylori* urease A or B subunits produced in *E. coli* and purified as described above, and coupled to hydroxyapatite crystals, used as a carrier to enhance M cell binding and uptake. Cholera toxin (Sigma) was given as a mucosal adjuvant. In this experiment, groups of female SPF BALB/c six-week old mice were each orally immunized with 30 µg of recombinant *Helicobacter pylori* urease A subunit, coupled to 1 mg of hydroxyapatite plus 10 µg of cholera toxin adjuvant at day 0, 8, 14 and 21. The mice were then challenged with $10^8$ *H. felis*, at day 32, 34 and 36. For comparison purposes, similar female SPF BALB/c six-week old mice were orally immunized with 30 µg of recombinant *Helicobacter pylori* urease B subunit coupled to hydroxyapatite plus 10 µg cholera toxin at day 0, 8, 14 and 21. The mice were challenged three times, at day 32, 34 and 36, with *H. felis*. As a control, female SPF BALB/c six-week old mice were each orally sham-immunized with 10 µg of cholera toxin and 1 mg of hydroxyapatite at day 0, 8, 14 and 21. The mice were then challenged at day 32, 34 and 36 with *H. felis*. All mice subject to the study were immunized and challenged in parallel. Animals were sacrificed on day 48 (12 days after challenge) or 10 weeks after challenge.

D. Analysis of Gastric Biopsies, Blood, and Intestinal Secretions

Biopsies were taken from the stomach and blood was obtained from the heart. The intestines were removed and washed with 1 mM PMSF (Boeringher) in PBS buffer to obtain intestinal secretions for ELISA analysis.

To evaluate protection against *H. felis* colonization, gastric biopsies from each animal were screened for the presence of *H. felis* by assessing rapid urease activity by the Jatrox HP test (Rohm Pharma), according to the supplier's directions. Briefly, gastric biopsies are immersed in 0.5 ml supplier's mixture of urea and phenol red, a pH indicator. A non-commercial version of the urea and phenol red mixture will be recognized by those skilled in the art and may contain, for example, Bacto yeast extract (0.1 g), monopotassium phosphate (0.091 g), disodium phosphate (0.095 g), urea (20 g), and Bacto phenol red (0.01 g) at a final pH of 6.9 at 25° C. Urease activity generates ammonia and bicarbonate from urea, and is followed by the calorimetric change of the solution towards a higher absorbance at 550 nm. Urease activity was quantified by spectrophotometric analysis. Other methods of assaying urease activity will be recognized by those skilled in the art and may be found in, for example, Mobley, H. L. T. & Hausinger, R. P., "Microbial Ureases: Significance, Regulation, and Molecular Characterization," Microb. Reviews, Vol. 53, 85–108 (1989).

Gastric biopsies of each animal included in the experiment described in section B were also cultured on BHI agarose plates, supplemented as above, for the detection of *H. felis*. After incubation for 3 to 10 days in microaerophilic conditions, the presence of *H. felis* was confirmed by Gram staining and determination of urease activity. As a very significant correlation was obtained for the detection of *H. felis* in gastric biopsies between urease tests and *H. felis* cultures during the first set of experiments (see Table 3), only gastric biopsy urease tests were performed for the detection of *H. felis* in the experiment described in section C. Detection of *H. felis* was confirmed by microscopy by two independent investigators, using two different colorations (acridine orange and cresyl violet).

Blood samples were allowed to clot for 3 hours at RT (room temperature), and serum harvested and frozen at −20° C., until further analysis. Intestinal secretions were spun for 5 minutes at 4° C. to remove debris, and kept frozen at −20° C. Serum and intestinal samples of each animal were analyzed by ELISA for evaluation of anti-Helicobacter activity, according to standard procedures. Briefly, 96-well plates were coated with a sonicate of *Helicobacter pylori*, followed by saturation with 5% fat-free milk. Samples were serially diluted from 1:1 to 1:1000 and incubated overnight at 4° C. on ELISA plates. Biotinylated anti-mouse IgG (serum) and anti-mouse IgA, followed by streptavidin-Horseradish peroxidase was used for the determination of the antibody levels.

Figure 3:
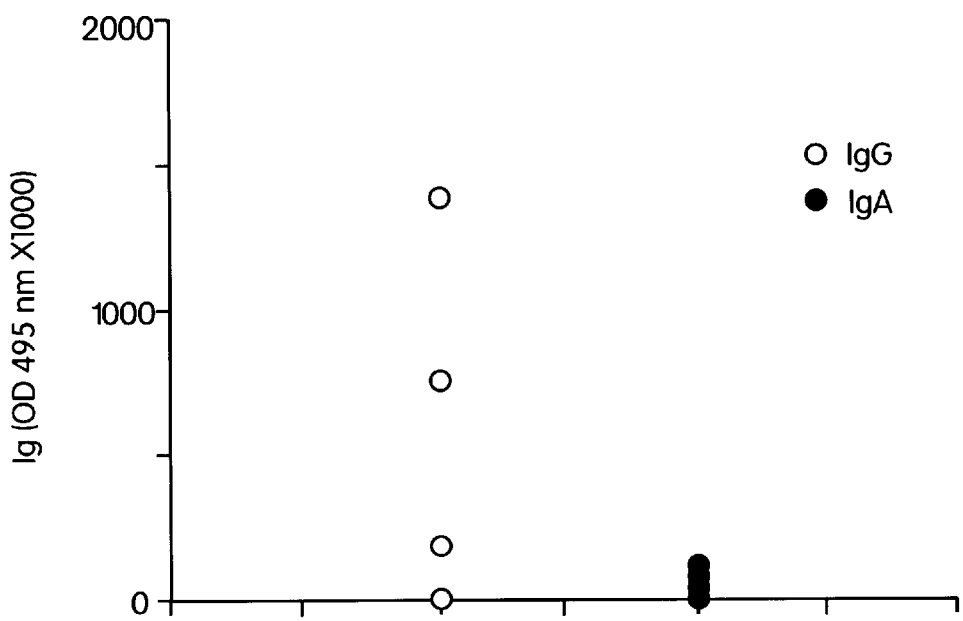
Figure 4:
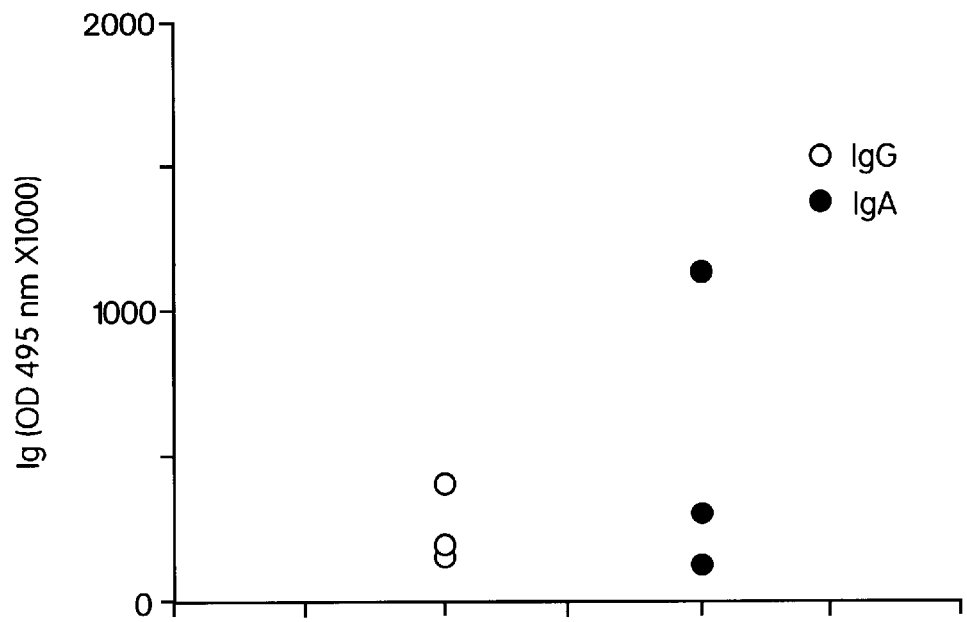
Figure 5:
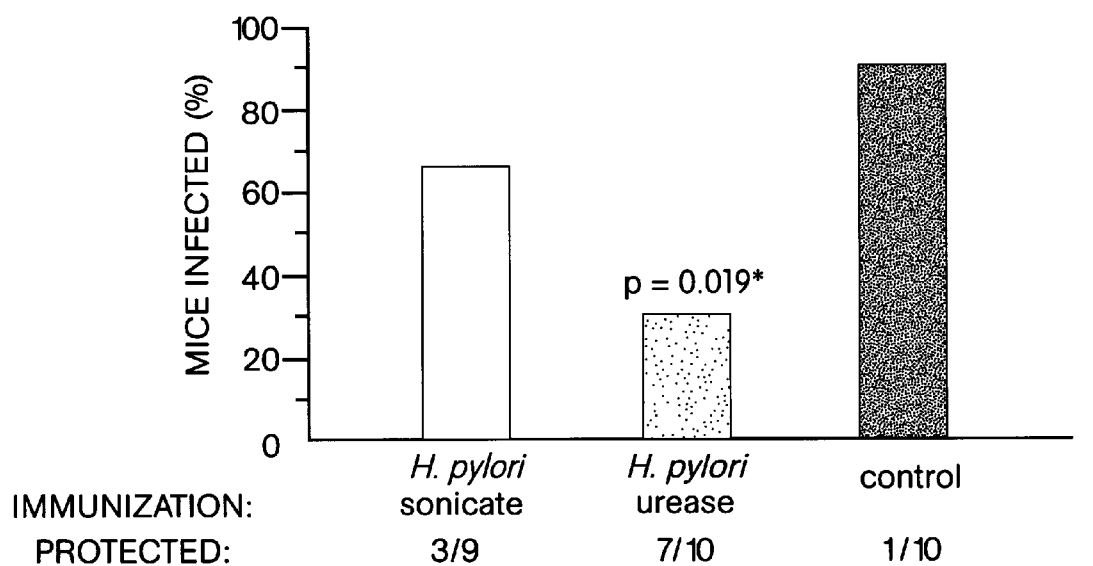
Figure 6A:
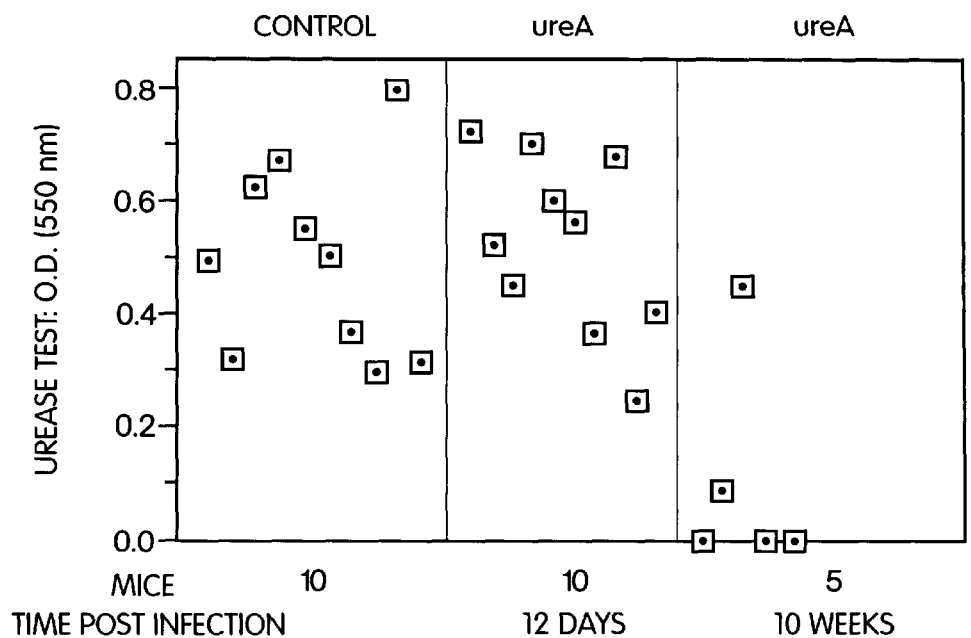
Figure 6B:
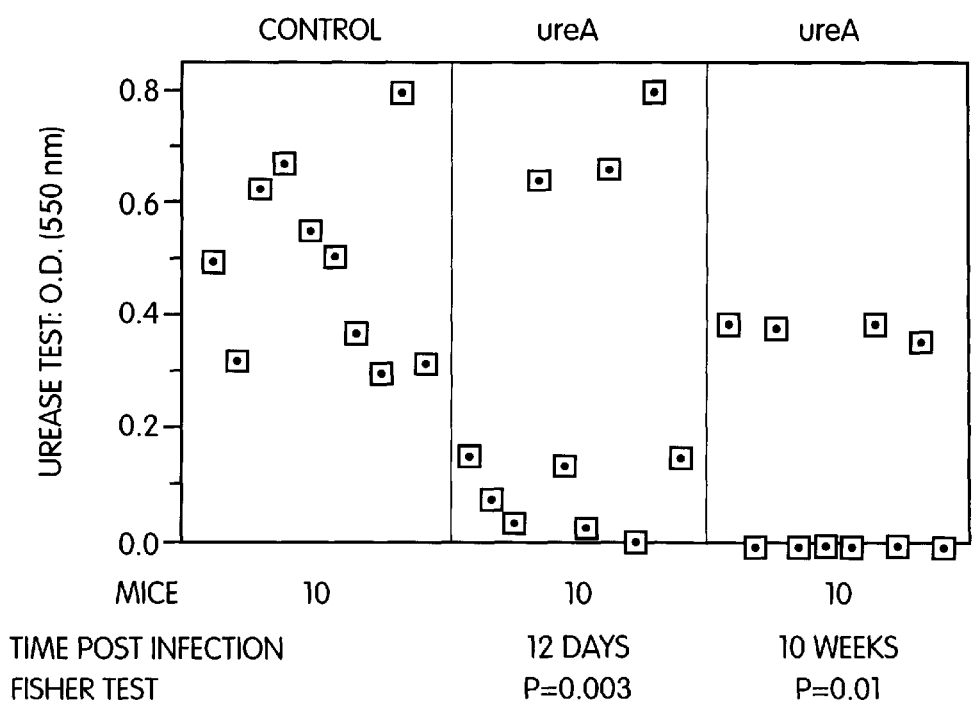

The results of *H. felis* challenges following immunizations with purified *Helicobacter pylori* urease are set out in Tables 1–3 and FIGS. 1–4 and the results of *H. felis* challenges following immunizations with recombinant *Helicobacter pylori* urease A and B subunits are set out in Tables 4–6 and FIGS. 5 and 6.

TABLE 1

| mouse number | Immunization | urease test 12 h | culture Gram | Immunoglobulins Serum | | Intestinal secretion | |
|---|---|---|---|---|---|---|---|
| | | | | Ig | Ig G | Ig | IgA |
| 1 | Urease + HF | + | H felis | 27 | 0 | 25 | 258 |
| 2 | Urease + HF | 0 | 0 | 264 | 273 | 221 | 246 |
| 3 | Urease + HF | 0 | 0 | 84 | 44 | 318 | 354 |
| 4 | Urease + HF | + | H felis | 81 | 42 | 12 | 5 |
| 5 | Urease + HF | 0 | 0 | 98 | 137 | 126 | 234 |
| 6 | Urease + HF | + | 0 | 968 | 2093 | 31 | 22 |
| 7 | Urease + HF | 0 | 0 | 98 | 0 | 96 | 34 |
| 8 | Urease + HF | 0 | 0 | 247 | 1010 | 214 | 128 |
| 9 | Urease + HF | 0 | 0 | N.D. | N.D. | 48 | 23 |
| 10 | Urease + HF | 0 | 0 | 50 | 0 | 124 | 99 |
| 11 | Urease | 0 | 0 | 319 | 205 | 44 | 53 |
| 12 | Urease | 0 | 0 | 14 | 0 | 86 | 87 |
| 13 | Urease | 0 | 0 | 0 | 0 | 0 | 0 |
| 14 | Urease | 0 | 0 | 0 | 0 | 43 | 61 |
| 15 | Urease | 0 | 0 | 58 | 0 | 110 | 127 |
| 16 | Urease | 0 | 0 | 140 | 63 | 21 | 37 |
| 17 | Urease | 0 | 0 | 84 | 240 | 114 | 280 |
| 18 | Urease | 0 | 0 | N.D. | N.D. | 93 | 148 |
| 19 | Urease | 0 | 0 | 45 | 0 | 135 | 216 |
| 20 | Urease | 0 | 0 | 261 | 197 | 161 | 261 |
| 21 | CT + HF | 0 | 0 | 0 | 0 | 0 | 2 |
| 22 | CT + HF | + | H felis | 63 | 0 | 310 | 303 |
| 23 | CT + HF | + | H felis | 90 | 0 | N.D. | N.D. |
| 24 | CT + HF | + | H felis | 31 | 0 | 150 | 192 |
| 25 | CT + HF | + | H felis | 197 | 250 | 250 | 440 |
| 26 | CT + HF | + | H felis | 105 | 135 | 214 | 138 |
| 27 | CT + HF | + | H felis | 140 | 47 | 109 | 55 |
| 28 | CT + HF | + | 0 | 0 | 0 | 16 | 15 |
| 29 | CT + HF | + | H felis | 0 | 0 | 0 | 0 |
| 30 | CT + HF | + | H felis | N.D. | N.D. | N.D. | N.D. |
| 31 | HP sonicate + HF | + | H felis | 0 | 0 | 76 | 103 |
| 32 | HP sonicate + HF | + | H felis | 77 | 0 | 11 | 33 |
| 33 | HP sonicate + HF | + | H felis | 549 | 748 | 57 | 36 |
| 34 | HP sonicate + HF | 0 | 0 | 660 | 153 | 180 | 286 |
| 35 | HP sonicate + HF | + | H felis | 730 | 192 | 0 | 5 |
| 36 | HP sonicate + HF | + | H felis | 32 | 0 | 5 | 64 |

TABLE 1-continued

| mouse number | Immunization | urease test 12 h | culture Gram | Immunoglobulins Serum | | Intestinal secretion | |
|---|---|---|---|---|---|---|---|
| | | | | Ig | Ig G | Ig | IgA |
| 37 | HP sonicate + HF | 0 | 0 | 400 | 400 | 312 | 1149 |
| 38 | HP sonicate + HF | + | H felis | 1007 | 1360 | 149 | 26 |
| 39 | HP sonicate + HF | 0 | 0 | 220 | 186 | 133 | 122 |
| 40 | HP sonicate | 0 | 0 | 873 | 1016 | 352 | 514 |
| 41 | HP sonicate | 0 | 0 | 727 | 899 | 126 | 191 |
| 42 | HP sonicate | 0 | 0 | 109 | 68 | 44 | 83 |
| 43 | HP sonicate | 0 | 0 | 147 | 949 | 167 | 97 |
| 44 | HP sonicate | 0 | 0 | 845 | 1094 | 246 | 64 |
| 45 | HP sonicate | 0 | 0 | 1217 | 1198 | 210 | 157 |
| 46 | HP sonicate | 0 | 0 | 81 | 0 | 256 | 218 |
| 47 | HP sonicate | 0 | 0 | 329 | 210 | 241 | 276 |
| 48 | HP sonicate | 0 | 0 | 1049 | 737 | 197 | 211 |

In Table 1, which refers to the experiment described in section B, "h" means hour, "Ig" means immunoglobulin, "ND" means "not determined", "urease+HF" means that the mice were immunized with urease (coupled to hydroxyapatite, with cholera toxin) and then challenged with *H. felis*, "urease" means that the mice were immunized with urease (coupled to hydroxyapatite, with cholera toxin) and not challenged, "CT+HF" means that the mice were sham-immunized with cholera toxin and challenged with *H. felis*, "HP sonicate+HF" means that the mice were immunized with *Helicobacter pylori* sonicate with cholera toxin and challenged by *H. felis*, and "HP sonicate" means that the mice were immunized with *Helicobacter pylori* sonicate with cholera toxin and not challenged. In Table 1, the numbers for the antibody results are given as a measure of absorbance at 595 nm multiplied by 1000. The background measured in absence of the antibodies, was subtracted.

The results of experiment described in section B obtained on the basis of the gastric biopsies urease tests and on Gram staining of *H. felis* cultures are set out in Table 2. Infection was defined by mice with one or more markers of colonization by *H. felis*, including urease test or Gram staining of cultures.

TABLE 2

| Immunization | Challenge | % infected | % protected |
|---|---|---|---|
| Urease | H. felis | 3/10 (30%) | 7/10 (70%)* |
| Sonicate | H. felis | 6/9 (66%) | 3/9 (33%)** |
| CT | H. felis | 9/10 (90%) | 1/10 (10%) |

*p = 0.0198 (two tailed Fisher exact test) compared to CT control
**p = 0.303 (two tailed Fisher exact test) compared to CT control It will be seen from the results set out in Tables 1 and 2 that statistically significant protection against *H. felis* challenge is obtained with oral immunization using *Helicobacter pylori* urease as compared to that obtained using either *Helicobacter pylori* sonicate or cholera toxin. Referring to Table 2, it will be seen that from a total of 10 immunized animals, only 3 became infected, as compared to 6 of the animals immunized with *Helicobacter pylori* sonicate and 9 of the animals immunized with cholera toxin. Table 2 shows that 70% of the animals were protected from challenge by *H. felis* as compared to 33% of the animals immunized with *Helicobacter pylori* sonicate and 10% of the animals immunized with cholera toxin and then subjected to *H. felis* challenge. In other words, 90% of the control mice exposed to H. felis became infected by that pathogen whereas, in contrast, in mice immunized with Helicobacter pylori urease 28 days before exposure to H. felis, the infection rate was only 30%. This represents a significant reduction in infection (p=0.0198 in the Fisher exact test, as compared to the control mice). When the mice were orally immunized with Helicobacter pylori sonicate, the infection rate was 67% (not significant versus the control). The protection obtained using Helicobacter pylori urease is unexpected and could not have been predicted on the basis of the results observed using Helicobacter pylori sonicate.

Figure 2:
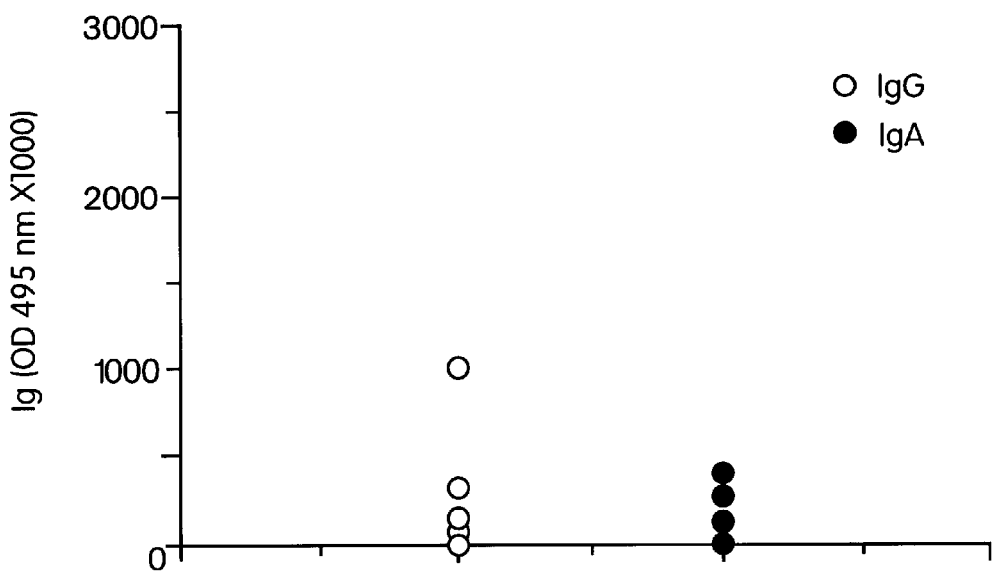

Referring to FIGS. 1–4, FIG. 1 represents graphically the results of tests for antibodies in serum (IgG) and intestinal secretion (IgA) in mice not protected after immunization with urease. These are mice numbers 1, 4 and 6 appearing in Table 1, and constitute Group A. FIG. 2 shows the antibody responses of mice that were protected after immunization with urease (Group B), i.e. mice 2, 3, 5 and 7–10.

FIGS. 3 and 4 relate to the results obtained with mice numbers 31–39. FIG. 3 (Group C) depicts antibody responses of mice not protected after immunization with Helicobacter pylori sonicate (mice numbers 31, 32, 33, 35, 36 and 38) and FIG. 4 (Group D) depicts the antibody responses of mice protected after immunization with Helicobacter pylori sonicate (mice numbers 34, 37 and 39). It is of interest to note with respect to FIGS. 3 and 4 that the IgA antibody responses (but not IgG) are higher in the mice exhibiting protection than in the mice that are not protected, suggesting a correlation between protection and IgA response. Serum IgG responses did not exhibit a correlation. Mucosal IgA but not serum IgG are known to play a role in protection against bacterial infections of the gut. (McGhee, J. R and Kyono, H. "New Perspectives in Vaccine Development: Mucosal Immunity to Infections" Infect Agents Dis., vol. 2, 55–73 (1993)).

The results of the correlation between the detection of H. felis in gastric biopsies by urease tests and by cultures are set out in Table 3.

TABLE 3

|  | Urease Test + | Urease Test − | Total |
|---|---|---|---|
| H. felis culture (+) | 16 | 0 | 16 |
| H. felis culture (−) | 2 | 30 | 32 |
| Total | 18 | 30 | 48 |

Two-tailed Fisher's Exact Test: p<0.00001

Table 3 shows that a very significant correlation exists between the results of urease tests performed on gastric biopsies and the identification of H. felis by cultures. All animals shown in Table 3 that were positive for urease activity, were H. felis positive by histopathology. As cultures detected less often H. felis infection than urease tests, urease tests were preferred for the diagnosis of H. felis infection in mice in the next experiments, due to its better sensitivity. This approach allowed the duplication of urease tests with larger fragments of the stomach of each mouse, and a further increase in the sensitivity of the urease test. Furthermore, the use of the method with the highest sensitivity prevent an overestimation of the protection obtained by the vaccine preparation to be tested. When positive culture is used as the standard for infection, the protection induced after urease immunization during the experiment depicted in section B is as significant as with the combined use of urease test and culture (p=0.021 versus p=0.019).

The results of the experiments described in section C (recombinant urease subunits), obtained on the basis of the gastric biopsies urease tests, are set out in Table 4, 5 and 6 and depicted in FIG. 6.

TABLE 4

| immunization | mice no | Urease test | Infection |
|---|---|---|---|
| CT | 20 | 0.49 | + |
| Sacrificed 12 days | 21 | 0.31 | + |
| post challenge | 22 | 0.62 | + |
|  | 23 | 0.67 | + |
|  | 24 | 0.55 | + |
|  | 50 | 0.50 | + |
|  | 51 | 0.37 | + |
|  | 52 | 0.29 | + |
|  | 53 | 0.79 | + |
|  | 54 | 0.32 | + |
| ure A + HAP + CT | 40 | 0.67 | + |
| Sacrificed 12 days | 41 | 0.48 | + |
| post challenge | 42 | 0.42 | + |
|  | 43 | 0.65 | + |
|  | 44 | 0.56 | + |
|  | 45 | 0.52 | + |
|  | 46 | 0.33 | + |
|  | 47 | 0.63 | + |
|  | 48 | 0.22 | + |
|  | 49 | 0.37 | + |
| ure B + HAP + CT | 25 | 0.15 | − |
| Sacrificed 12 days | 26 | 0.07 | − |
| post challenge | 27 | 0.03 | − |
|  | 28 | 0.64 | + |
|  | 29 | 0.13 | − |
|  | 30 | 0.02 | − |
|  | 31 | 0.66 | + |
|  | 32 | 0.00 | − |
|  | 33 | 0.79 | + |
|  | 34 | 0.15 | − |
| ure A + HAP + CT | 68 | 0.00 | − |
| Sacrificed 10 weeks | 69 | 0.07 | − |
| post challenge | 70 | 0.42 | + |
|  | 71 | 0.00 | − |
|  | 72 | 0.00 | − |
| ure B + HAP + CT | 73 | 0.37 | + |
| Sacrificed 10 weeks | 74 | 0.00 | − |
| post challenge | 75 | 0.37 | + |
|  | 76 | 0.00 | − |
|  | 77 | 0.00 | − |
|  | 78 | 0.00 | − |
|  | 79 | 0.39 | + |
|  | 80 | 0.00 | − |
|  | 81 | 0.37 | + |
|  | 82 | 0.00 | − |

In Table 4, "CT" means cholera toxin; "UreA" means recombinant Helicobacter pylori urease A subunit; "Ure B" means recombinant Helicobacter pylori urease B subunit; and "HAP" means hydroxyapatite crystals. Mice 20 to 54 were sacrificed 12 days post challenge and mice 68 to 82 10 weeks (106 days) post challenge. The results of the urease test performed from biopsies of the stomach of each animal are expressed as OD values at 550 nm. The O.D. value for the assay solution alone (0.075 O.D.) was subtracted as background from the O.D. value obtained for each mouse. The positive and negative signs depicts the final status of infection of each animal, according to the positivity or negativity of the urease test for detection of H. felis. Positivity: $OD_{550}$ values >0.2. The 0.2 value was chosen to define a positive infection because at this value, the color change to the Jatrox solution could be observed with the naked eye.

TABLE 5

Protection as measured 12 days post challenge

| Immunization | Challenge | % infected | % protected |
|---|---|---|---|
| Urease A subunit | H. felis | 10/10 (%) | 0/10 (0%) |
| Urease B subunit | H. felis | 3/10 (30%) | 7/10 (70%)* |
| CT | H. felis | 10/10 (100%) | 0/10 (0%) |

*p = 0.0031 (two tailed Fisher exact test) compared to CT control

TABLE 6

Protection as measured 10 weeks post challenge

| Immunization | Challenge | % infected | % protected |
|---|---|---|---|
| Urease A subunit | H. felis | 1/5 (20%) | 4/5 (80%)* |
| Urease B subunit | H. felis | 4/10 (40%) | 6/10 (60%)** |

*p = 0.003 (two tailed Fisher exact test) compared to CT control
**p = 0.01 (two tailed Fisher exact test) compared to CT control It will be seen from the results set out in Tables 4, 5 and 6 that statistically significant protection against H. felis challenge is obtained with oral immunization using recombinant Helicobacter pylori urease B subunit as compared to that obtained using either recombinant Helicobacter pylori urease A subunit or cholera toxin. Referring to Table 4, it will be seen that, 12 days post challenge, from a total of 10 immunized animals, only 3 were found infected in the urease B subunit group, as compared to all 10 animals immunized with Helicobacter pylori A subunit of urease and 10 out of 10 of the animals immunized with cholera toxin. Table 4 shows that 70% of the animals were protected from challenge by H. felis as compared to 0% of the animals immunized with Helicobacter pylori urease A subunit and 0% of the animals immunized with cholera toxin and then subjected to H. felis challenge. In other words, 100% of the control mice challenged with H. felis became infected whereas, in mice immunized with recombinant Helicobacter pylori urease B subunit the infection rate was only 30%. This represents a significant reduction in infection (p=0.0031, Fisher exact test) as compared to the control mice. The fact that the protection observed with Helicobacter pylori urease is entirely conferred by immunization with the B subunit of urease, and that the A subunit has no such effect, was not expected on the basis of our experiment with purified urease. This definition of the roles of the 2 structural subunits of urease in the development of a protective immune response is therefore novel. The protection obtained using recombinant urease subunits, which are enzymatically inactive, also teaches that non toxic forms of urease can be used as oral vaccine against Helicobacter infection. Furthermore these results strongly suggest that recognition of the active site is not required for protection, as an inactive urease B subunit is very unlikely to induce antibodies that will recognize and inhibit the catalytic site of native urease.

Referring to Table 6, it will be seen that, when mice are sacrificed 10 weeks post infection, 60% (6 mice out of 10) of the animals immunized with urease B subunit and 80% (4 mice out 5) of the animals immunized with Helicobacter pylori urease A subunit were protected against H. felis infection. The fact that protection obtained through immunization with urease B subunit lasts over time and that immunization with urease A induces a protection which is delayed compared to the one induced by urease B subunit could not be expected from our experiment with purified urease or with other experiment performed earlier. The fact that urease A subunit immunization confers protection definitively proves that recognition of the active site is not required for protection.

FIG. 6 summarizes results obtained after oral immunization with recombinant urease A and B subunits (described in Table 5 and 6).

A second set of mice was immunized and assayed for infection with Helicobacter felis at 10 weeks post challenge according to the protocol described in Section C. In this example, twelve mice were sham immunized with cholera toxin alone, twelve mice were immunized with recombinant ure A subunit, and ten mice were immunized with recombinant ure B subunit. The mean urease activity level found in stomach samples mice that were immunized with ure B, but not infected (uninfected mice controls), was 0.045, and this amount was subtracted as background from each O.D. value obtained. Mice were considered to be infected when the O.D. value was greater than twice the standard deviation of values obtained with the uninfected mice controls; the standard deviation was 0.022. The data obtained from this experiment is presented in Table 7.

TABLE 7

| immunization | mice no. | Urease test | Infection |
|---|---|---|---|
| CT | 135 | 0.40 | + |
| Sacrificed 10 weeks | 136 | 0.28 | + |
| post challenge | 137 | 0.25 | + |
|  | 138 | 0.10 | + |
|  | 139 | 0.10 | + |
|  | 140 | 0.34 | + |
|  | 141 | 0.41 | + |
|  | 142 | 0.36 | + |
|  | 143 | 0.46 | + |
|  | 144 | 0.40 | + |
|  | 145 | 0.40 | + |
|  | 146 | 0.51 | + |
| ure A + HAP + CT | 161 | 0.12 | + |
| Sacrificed 10 weeks | 162 | 0.47 | + |
| post challenge | 163 | 0.00 | − |
|  | 164 | 0.00 | − |
|  | 165 | 0.02 | − |
|  | 166 | 0.01 | − |
|  | 167 | 0.01 | − |
|  | 168 | 0.37 | + |
|  | 169 | 0.00 | − |
|  | 170 | 0.39 | + |
|  | 171 | 0.47 | + |
|  | 172 | 0.00 | − |
| ure B + HAP + CT | 151 | 0.00 | − |
| Sacrificed 10 weeks | 152 | 0.00 | − |
| post challenge | 153 | 0.00 | − |
|  | 154 | 0.03 | − |
|  | 155 | 0.00 | − |
|  | 156 | 0.00 | − |
|  | 157 | 0.02 | − |
|  | 158 | 0.00 | − |
|  | 159 | 0.01 | − |
|  | 160 | 0.00 | − |

Using this alternative method of analysis, the data presented in Table 4 was reanalyzed along with the data in Table 7. Instead of subtracting the background O.D. value obtained with the urease assay solution alone (0.075 O.D.), the mean urease level obtained from the uninfected mice controls was used as the background level.

The mean urease level obtained from uninfected mice sacrificed at twelve days was 0.089. Mice numbered 20–54 were considered infected when the O.D. value was greater than twice the standard deviation of values obtained with the uninfected mice controls; the standard deviation was 0.008. The background level subtracted from the O.D. values of mice sacrificed at ten weeks was 0.045, and mice were considered infected when the O.D. value was greater than 0.044.

Using this alternative method of analysis, at twelve days post challenge, no effect was seen after sham immunization or after immunization with the ure A subunit. However, only a low-grade infection (O.D. value<0.22) was observed in 70% of the animals immunized with the ure B subunit (p<0.02, Mann-Whitney U-test, compared to sham immunized control). When mice were sacrificed ten weeks post challenge, 59% (10/17) of the mice immunized with the ure A subunit were protected against *H. felis* infection (p=0.0019, two-tailed Fisher's exact test, when compared to sham-immunized mice). Furthermore, 80% (16/20) of the mice immunized with the ure B subunit were protected against *H. felis* infection (p=0.00002, two-tailed Fisher's exact test, when compared to control, sham-immunized mice). Under this alternative analysis, the ure A subunit also elicits protective immunity. Under either method of analysis, the results obtained demonstrate that immunization with recombinant *Helicobacter pylori* urease subunits elicits protective immunity against Helicobacter infection.

EXAMPLES

The invention will now be further described by reference to the following non-limiting examples.

a) The Bacterial Strains

*H. felis* was provided by J. Fox (Division of Comparative Medicine, Mass. Institute of Technology, Boston, USA). *Helicobacter pylori* was isolated from patients with ulcer disease (CHUV, Lausanne, Switzerland).

b) Bacterial Cultures

Liquid Culture—Bacteria were cultured on BHI (Brain-Heart Infusion, BioMerieux) liquid medium containing 0.25% of yeast extract (Difco) and 10% of fetal calf serum (Inotech) supplemented with 0.4% of Campylobacter selective complement (Oxoid). The bacteria were incubated under microaerophilic conditions at 37° C. and shaken at 37° C. for 2 to 3 days.

Frozen Culture—The bacteria were cultured in liquid media, then assayed for urease activity, and evaluated for morphology by Gram staining and for motility by microscopy. The bacteria were then centrifuged and resuspended at a concentration of 30 O.D. per ml in BHI plus 20% glycerol and frozen at −80° C. Just before use, frozen stocks were thawed on ice, washed in 20 ml BHI, centrifuged, and resuspended at a concentration of 1 O.D. to 1.5 O.D. per 200 $\mu$l in 5 mM NaHCO$_3$.

Culture on Agarose plates—The bacteria were cultured on agar plate consisting on BHI with 0.25% of yeast extract and 5% of sheep blood under microaerophilic conditions at 37° C. for 3 days.

Quantification—The quantity of bacteria was determined by the optical density of the BHI solution at 660 nm (1 optical density unit (O.D.) corresponding to $10^8$ bacteria). The number of viable bacteria is measured on the number of colony forming units.

c) Preparation of Sonicates

*Helicobacter pylori* was collected from 31 blood agar plates in 0.15 M NaCl and spun 5 minutes at 1400 g at 4° C. The pellet was resuspended in 3 ml of NaCl and sonicated for 4 minutes. The amount of proteins was evaluated by a Bradford assay (BioRad Kit according to supplier).

d) Coupling of Immunogen to Hydroxyapatite

Immunogen (urease or subunit thereof) was incubated for 1 hour at 4° C. with hydroxyapatite. 1.0 mg of hydroxyapatite was used for 30 $\mu$g of immunogen per mouse. At the end of the incubation, 10 $\mu$g of cholera toxin was added in a final volume of 200 $\mu$l PBS.

e) Challenge with *Helicobacter felis*

Mice were lightly anesthetized prior to intragastric challenge with *Helicobacter felis*. *H. felis* in a total volume of 200 $\mu$l were delivered to the stomachs of the respective mice using silicon tubing attached to a hypodermic syringe.

Example 1 a) Extraction

*Helicobacter pylori* from 30 blood agar plates was harvested in 0.15 M NaCl on ice. The solution was spun 5 minutes at 1400 g at 4° C. The pellet was resuspended in 20 ml of H$_2$O and vortexed for 45 seconds (maximum speed). The extract was then spun 20 minutes at 6700 g at 4° C. The supernatant was recovered and the quantity of protein was evaluated (see "Quantification" above) and precipitated with 70% of ammonium sulfate.

b) Purification of Urease

The solution was chromatographed on a Sepharose CL-6B column (Pharmacia) with PBS (phosphate buffered saline) as mobile phase. The 22 collected fractions which presented a strong urease activity were pooled and dialyzed overnight at 4° C. against 3 liters of PEB (20 mM phosphate buffer, pH 7) and then chromatographed on a Q Sepharose fast flow (Pharmacia) with PEB as mobile phase. The fractions were eluted by 0 to 500 mM NaCl gradient. Ten of the collected fractions with a strong urease activity were individually subjected to an SDS gel followed by a Coomassie staining. The 6 fractions presenting 2 distinct bands corresponding to MW-63 and −28 KDa were pooled and were considered as the purified urease.

Example 2 (see also section B)

Mice employed in the immunization studies were lightly anesthetized with ether prior to intragastric immunization. And then, sonicate preparation or purified urease, hydroxyapatite and cholera toxin was suspended in PBS and 200 $\mu$l were delivered to the stomach of the respective mice using a polyethylene tubing attached to a hypodermic syringe. This procedure will be referred to as oral immunization.

Three oral immunization protocols were evaluated. These are described below.

Protocol B1—Vaccination with Purified Urease

Female BALB/c six-week old mice (20) were orally immunized with 30 $\mu$g of purified of *Helicobacter pylori* urease and 1 mg of hydroxyapatite and 10 $\mu$g of cholera toxin at day 0, 7, 14 and 21. Ten mice were challenged at day 28 and 30 with $5\times10^7$ and $10^8$ *H. felis* from liquid culture.

Protocol B2—Vaccination with Helicobacter Sonicates

Female BALB/c six-week old mice (20) were orally immunized with 2 mg of *Helicobacter pylori* sonicate solution at day 0, 7, 14 and 21. Ten mice were challenged at day 28 and 30 with $5\times10^7$ and $10^8$ *H. felis*.

Protocol B3—Control

Female BALB/c six-week old mice were orally immunized with 1 mg hydroxyapatite and 10 $\mu$g of cholera toxin at day 0, 7, 14 and 21. The mice were challenged at day 28 and 30 with $5\times10^7$ and $10^8$ *H. felis*.

At day 35 all mice were sacrificed and biopsies from the stomach were taken as well as intestinal secretions and blood.

Protection and Evaluation

To evaluate protection, biopsies were screened for the urease activity by the Jatrox HP test (Rohm Pharma) according to the instructions of the supplier. The urease is quantified by a spectrophotometric measurement at 550 nm. The biopsies were also cultured for the presence of *H. felis* and the presence of *H. felis* was determined by Gram staining. Gastric antral biopsies were homogenized and diluted (1:10 and 1:1000) in 0.15 M NaCl and plated onto blood agar plates and incubated under microaerophilic conditions at 37° C. for 4 to 10 days.

Elisa

Intestinal secretions and blood were analyzed by ELISA for the evaluation of antibody titer. The ELISA was carried out as follows. Polystyrene plates (96 wells) were coated with 1ug/well of purified urease at 37° C. for 2 hrs. Non specific binding sites were blocked with 5% powdered milk in PBS 0.1% Tween at 37° C. for 30 minutes. The plates were washed once with PBS 0.1% Tween. Blood samples were tested at dilution 1:1000 and intestinal secretions 1:1. 100 µl of each sample were added to the antigen coated plates. After 2 hrs of incubation, plates were washed 3 times with PBS containing 0.1% Tween. Anti-mouse biotinylated whole antibody from goat and anti-mouse IgA, IgG and IgM biotinylated (Amersham) were added (100 µl) at dilution 1:500 except for IgA (1:250) and incubated at 37° C. for 1 hr. The plates were washed 3 times with PBS 0.1% Tween and 100 µl of 1:1000 dilution of streptavidin Horseradish peroxidase in PBS containing 0.1% Tween were added and incubated at 37° C. for 30 minutes. The plates ware washed 3 times and 50 µl of 1:50 dilution of o-phenyl-diamine in citrate buffer pH 5.0 with 1 µl/ml of 30% $H_2O_2$ were added and incubated at room temperature for 20 minutes. The absorbance at 495 nm was measured in each well.

Example 3 (see also section C)

Mice employed in the immunization studies were lightly anesthetized with ether prior to intragastric immunization. Then, 30 µg recombinant *Helicobacter pylori* urease A or B subunit produced in *E. coli*, bound with hydroxyapatite, and supplemented with cholera toxin was suspended in PBS and 200 µl were delivered to the stomach of the respective mice using a polyethylene tubing attached to a hypodermic syringe. This procedure will be referred to as oral immunization.

Three oral immunization protocols were evaluated. These are described below.

Protocol C1—Vaccination with Recombinant Urease A Subunit

Female BALB/c six-week old mice (10) were orally immunized with 30 µg of purified recombinant *Helicobacter pylori* urease A subunit and 1 mg of hydroxyapatite and 10 µg of cholera toxin at day 0, 8, 14 and 21. Ten mice were challenged at day 32, 34 and 36 with $10^8$ *H. felis* from liquid culture.

Protocol C2—Vaccination with Recombinant Urease B Subunit

Female BALB/c six-week old mice (10) were orally immunized with 30 µg of recombinant *Helicobacter pylori* urease B subunit and 1 mg of hydroxyapatite and 10 µg of cholera toxin at day 0, 8, 14 and 21. Ten mice were challenged at day 32, 34 and 36 with $10^8$ *H. felis* from liquid culture.

Protocol C3—Control

Female BALB/c six-week old mice were orally immunized with 1 mg of hydroxyapatite and 10 µg of cholera toxin at day 0, 8, 14 and 21. The mice were challenged at day 32, 34 and 36 with $10^8$ *H. felis*.

At day 42, or at day 106, mice were sacrificed and multiple biopsies from the stomach were taken.

Protection and Evaluation

To evaluate protection, biopsies of the corpus and antrum of the stomach were screened for urease activity by the Jatrox HP test (Rohm Pharma) according to the instructions of the supplier. The urease is quantified by a spectrophotometric measurement at 550 nm. The total of corpus and antrum OD values were added to obtain a final OD value for each mouse.

Example 4

To determine whether immunization with urease peptides would be an effective treatment of Helicobacter infection animals, mice were first challenged with *H. felis* and then immunized with *Helicobacter pylori* ure B subunit. The utility of immunization with *Helicobacter pylori* ure B subunit to treat Helicobacter infection is demonstrated in both Example 4 and Example 5.

a) Infection of Mice with *H. felis*

Female BALB/c six-to-eight week old mice were challenged with *H. felis* at days 1 and 3 with 1 O.D. of frozen culture. The mice were challenged at day 5 with 1.53 O.D. of liquid *H. felis* culture.

b) Vaccination with Recombinant *Helicobacter pylori* Urease B Subunit

Eight *H. felis* infected mice were orally immunized with 30 µg of recombinant *Helicobacter pylori* urease B subunit, 1 mg of hydroxyapatite and 10 µg of cholera toxin (holoenzyme obtained from Calbiochem) at days 23, 30, 37, and 44.

c) Controls

Ten *H. felis* infected mice were orally immunized with 1 mg of hydroxyapatite and 10 µg of cholera toxin at days 23, 30, 37, and 44. These mice were designated as "sham" immunized.

Figure 7:
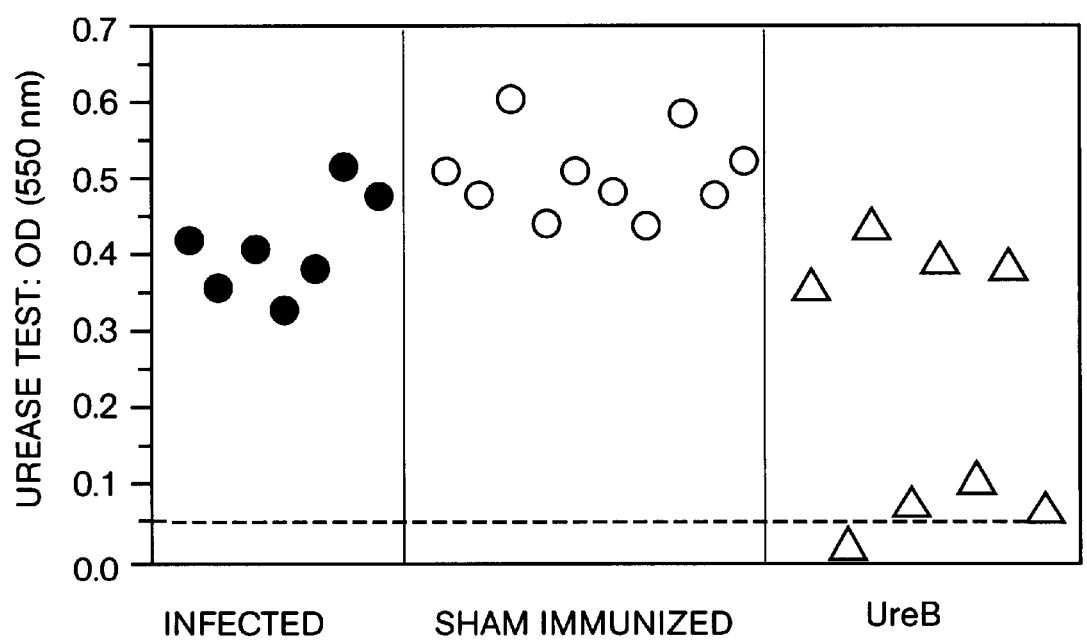

Seven *H. felis* infected mice were not subject to immunization.

d) Sacrifice and Evaluation At day 70 all mice were sacrificed. The stomachs were removed and cut in half longitudinally. To evaluate protection, one-half of the stomach of each mouse (both corpus and antrum sections) was screened for urease activity 3–4 hours post-sacrifice, by the Jatrox HP test (Rohm Pharma) according to the instructions of the supplier. The urease was quantitated by a spectrophotometric measurement at 550 nm. Ten naive (uninfected) BALB/c mice served as controls. These mice were sacrificed at day 70 and the stomach samples evaluated for urease activity to determine the background level of urease activity. The mean background value, 0.033 O.D., was subtracted from the O.D. value for each mouse. The standard deviation in urease activity among the naive mice was 0.025 O.D. The results of the urease assays are set out in Table 8 and depicted in FIG. 7. In FIG. 7, the dashed line indicates the O.D. value for twice the standard deviation in urease activity among the naive mice.

TABLE 8

| Treatment | Mouse No. | Urease test | Infection |
|---|---|---|---|
| Untreated | 1 | 0.42 | + |
| | 2 | 0.36 | + |
| | 3 | 0.41 | + |
| | 4 | 0.33 | + |
| | 5 | 0.38 | + |
| | 6 | 0.52 | + |
| | 7 | 0.48 | + |
| Sham (HAP + CT only) | 8 | 0.51 | + |
| | 9 | 0.48 | + |
| | 10 | 0.61 | + |
| | 11 | 0.44 | + |
| | 12 | 0.51 | + |
| | 13 | 0.48 | + |
| | 14 | 0.44 | + |
| | 15 | 0.58 | + |
| | 16 | 0.48 | + |
| | 17 | 0.53 | + |
| Ure B + HAP + CT | 18 | 0.36 | + |
| | 19 | 0.01 | − |
| | 20 | 0.43 | + |
| | 21 | 0.07 | +/− |
| | 22 | 0.39 | + |
| | 23 | 0.10 | +/− |
| | 24 | 0.38 | + |
| | 25 | 0.06 | +/− |

In Table 8, "ure B" means recombinant *Helicobacter pylori* urease B subunit as referenced above; "CT" means cholera toxin; and "HAP" means hydroxyapatite crystals; "untreated" means the mice were challenged with *H. felis*, but received no subsesequent immunization. The results of the urease test performed from biopsies of the stomach of each animal are expressed as O.D. values at 550 nm. The background value subtracted from the O.D. value for each mouse was 0.033. The infection is rated as positive (indicated by a "+") where the O.D. value at 550 nm is over twice the standard deviation found with the naive mouse controls (0.05 O.D.). A "+/−" indicates that the O.D. value is greater than background but less than 0.08, and that the value is reduced compared to the sham immunized controls.

It will be seen from the results set out in Table 7 and in FIG. 7 that administration of the *Helicobacter pylori* ure B subunit to mice infected with *H. felis* resulted in the clearance of infection in one out of eight mice. According to another, less conservative, interpretation of these results, defining a positive result as a value greater than 0.2, four out of eight mice (numbers 2, 4, 6, and 8) treated with ureB would be found to be protected from infection. However, under either of the two definitions of a positive result these mice exhibited a reduced urease activity as compared to the untreated and the sham-immunized mice. Using the 0.05 value to define infection, the level of infection in ure B immunized mice as compared to sham immunized mice exhibits a statistically significant (p value of less than 0.004) reduction in the level of infection. Thus the results of Example 4 indicate that administration of ure B to mice infected with *H. felis* results in a reduced level of infection.

Example 5 a) Infection of Mice with *H. felis*

Female BALB/c five-to-eight week old mice were challenged with *H. felis* at day 1 with 1 O.D. of liquid culture. The mice were challenged at day 3 with 0.8 O.D. *H. felis* cultured on agarose plates. The mice were challenged at day 5 with 1 O.D. of *H. felis* cultured on agarose plates.

b) Vaccination with Recombinant *Helicobacter pylori* Urease B Subunit

*H. felis* infected mice were orally immunized with 30 µg of recombinant *Helicobacter pylori* urease B subunit, 1 mg of hydroxyapatite and 10 µg of cholera toxin (holoenzyme obtained from Calbiochem) at days 23, 30, 37, and 44. These mice were designated as "immunized."

c) Controls

*H. felis* infected mice were orally immunized with 1 mg of hydroxyapatite and 10 µg of cholera toxin at days 23, 30, 37, and 44. These mice were designated as "sham" immunized.

d) Sacrifice and Evaluation

Figure 8A:
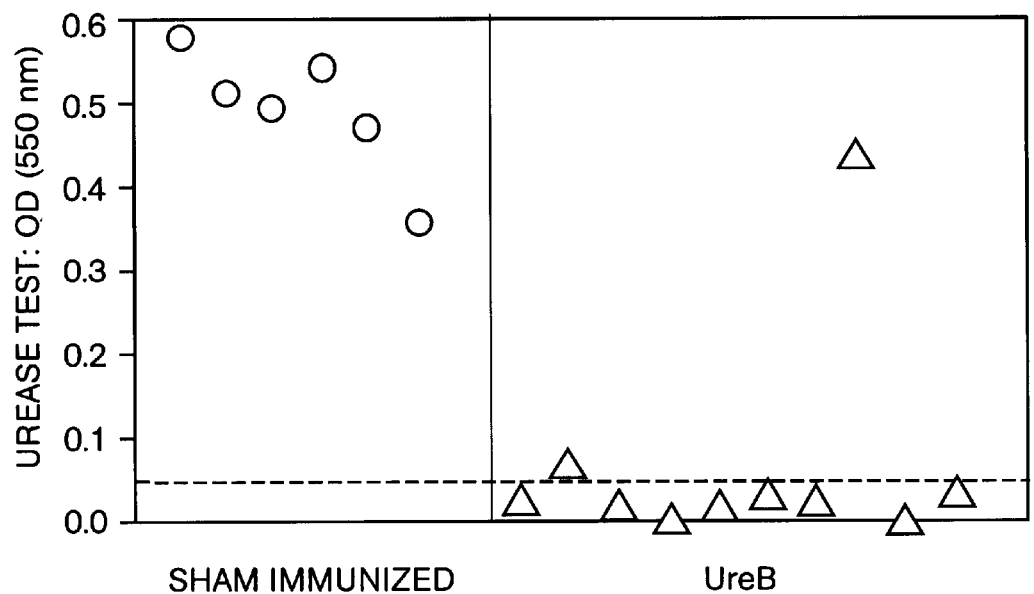
Figure 8B:
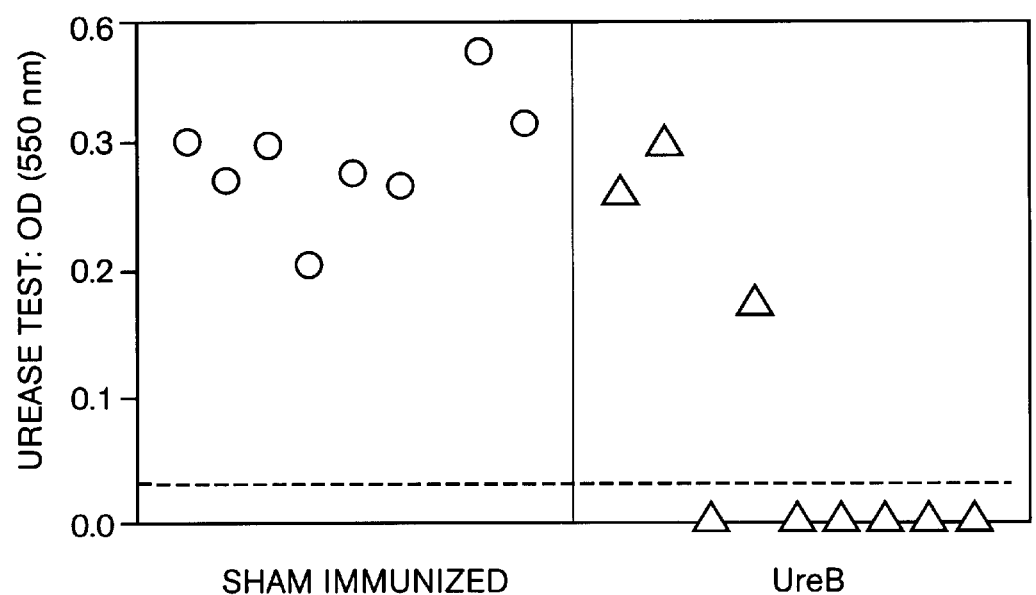

At day 62, ten immunized mice and six sham immunized mice were sacrificed. At eight weeks after the last immunization, ten immunized and eight sham immunized mice were sacrificed. Stomach samples were screened for urease activity as described in Example 4. The mean background found in 29 naive BALB/c mice, sacrificed at various times, was 0.04 O.D. This level of activity was used as a background measurement and subtracted from the O.D. value for each mouse. The standard deviation in urease activity among the naive mice was 0.02 O.D. The results of the urease assays are set out in Table 9 and depicted in FIG. 8. In FIG. 8, the dashed line indicates the O.D. value for twice the standard deviation in urease activity among naive mice.

e) Analysis of Blood and Fecal Samples

Blood Sample Collection

Blood samples were allowed to clot for 3 hours at room termperature, and serum harvested and frozen at −20° C., until further analysis.

Fecal Pellet Collection

Fresh fecal pellets (3–8) were collected in 1.5 ml eppendorf tubes containing 500 µl of PBS +5% non-fat dry milk+protease inhibitors (AEBSF 0.2 mM, Aprotinin 1 µg/ml, Leupeptin 10 µM, Bestatin 3.25 µM). The samples were frozen at −20° C. until use. They were then thawed on ice, mashed, and centrifuged at 10,000 g for 10 minutes at 4° C. to yield a supernatant free of debris, and yellowish brown in appearance.

Elisa

Serum and fecal pellet samples of each animal were analyzed by ELISA for evaluation of anti-urease activity, according to standard procedures.

Fecal pellets and blood were analyzed by ELISA for the evaluation of antibody titer. Polystyrene plates (96 wells) were coated with 0.5 µg/well of purified recombinant urease at 37° C. for 2 hrs. Non specific binding sites were blocked with 5% powdered milk in PBS containing 0.1% Tween at 37° C. for 30 minutes. The plates were washed once with PBS containing 0.1% Tween. Blood samples were tested at a dilution of 1:200 and fecal pellets at a dilution of 1:1. 100 ul of each sample were added to the antigen coated plates. After 2 hrs of incubation, plates were washed 3 times with PBS containing 0.1% Tween. Anti-mouse biotinylated whole antibody from goat (Amersham) and anti-mouse IgA coupled to Horseradish peroxidase (Serotec) were added (100 µl) at a dilution of 1:500 and incubated at 37° C. for 1 hr. The plates were washed 3 times with PBS containing 0.1% Tween and, for blood samples only, 100 µl of a 1:500 dilution of streptavidin and Horseradish peroxidase in PBS containing 0.1% Tween were added and incubated at 37° C. for 30 minutes. The plates were washed 3 times and 50 µl of a 1:50 dilution of o-phenyl-diamine in citrate buffer, pH 5.0, with 1 µl/ml of 30% $H_2O_2$ were added and incubated at room temperature for 20 minutes. The absorbance at 495 nm was measured in each well.

For the evaluation of total IgAs in fecal pellets, the ELISA was carried out as described above except that the plates were coated with 1 μg/ml of goat anti-mouse IgA (SIGMA) and the fecal supernatant was tested at a 1:200 dilution.

TABLE 9

| Sacrifice | Treatment | Mouse No. | Urease test | Infection |
|---|---|---|---|---|
| 2.5 weeks | Sham | 1 | 0.58 | + |
| | (HAP + CT only) | 2 | 0.51 | + |
| | | 3 | 0.50 | + |
| | | 4 | 0.54 | + |
| | | 5 | 0.47 | + |
| | | 6 | 0.36 | + |
| | Ure B + HAP + CT | 7 | 0.02 | − |
| | | 8 | 0.06 | + |
| | | 9 | 0.01 | − |
| | | 10 | 0.00 | − |
| | | 11 | 0.02 | − |
| | | 12 | 0.02 | − |
| | | 13 | 0.02 | − |
| | | 14 | 0.44 | + |
| | | 15 | 0.00 | − |
| | | 16 | 0.03 | − |
| 8 weeks | Sham | 17 | 0.30 | + |
| | (HAP + CT only) | 18 | 0.27 | + |
| | | 19 | 0.29 | + |
| | | 20 | 0.20 | + |
| | | 21 | 0.27 | + |
| | | 22 | 0.27 | + |
| | | 23 | 0.37 | + |
| | | 24 | 0.31 | + |
| | ure B + HAP + CT | 25 | 0.26 | + |
| | | 26 | 0.30 | + |
| | | 27 | 0.00 | − |
| | | 28 | 0.17 | + |
| | | 29 | N.D. | |
| | | 30 | 0.00 | − |
| | | 31 | 0.00 | − |
| | | 32 | 0.00 | − |
| | | 33 | 0.00 | − |
| | | 34 | 0.00 | − |

TABLE 10

| Sacrifice | Treatment | % cleared |
|---|---|---|
| 2.5 weeks | ure B | 8/10 (80%)* |
| | sham | 0/6 |
| 8 weeks | ure B | 6/9 (67%)** |
| | sham | 0/9 |

*p = 0.007 (two-tailed Fisher exact test) compared to sham control
**p = 0.014 (two-tailed Fisher exact test) compared to sham control In Tables 9 and 10, "ure B' means recombinant *Helicobacter pylori* urease B subunit as referenced above; "CT" means cholera toxin; and "HAP" means hydroxyapatite crystals. "sacrifice" means the date of sacrifice as measured from the last immunization at day 44. "N.D." indicates that no data were available. The results of the urease test performed from biopsies of the stomach of each animal are expressed as O.D. values rated at 550 nm. The infection is rated as positive (indicated by a "+") where the O.D. value at 550 nm is over twice the standard deviation found in the mature mice (0.04 O.D.). The background value subtracted from the O.D. value for each mouse was 0.04 O.D. In Table 10, "% cleared" indicates clearance of infection as measured by the urease assay.

It will be seen from the results set out in Tables 9 and 10, and in FIG. 8, that administration of the *Helicobacter pylori* ure B subunit to mice infected with *H. felis* resulted in the clearance of infection in eight out of ten mice as assayed when the mice were sacrificed 2.5 weeks after the last immunization. When the assay was performed when the mice were sacrificed eight weeks after the last immunization, the infection was cleared in six out of nine mice. If the higher value of 0.2 is chosen to define infection as referred to in the discussion of Table 8, under this method of interpretation, treatment with the ure B subunit resulted in clearance of infection in nine out of ten mice sacrificed at 2.5 weeks.

Table 10 indicates that statistically significant therapeutic treatment of *H. felis* infection is obtained with oral immunization using recombinant *Helicobacter pylori* urease B subunit as compared to that obtained by sham immunization with cholera toxin and hydroxyapatite alone. Table 10 shows that, when measured at 2.5 weeks after the last immunization, 80% of the infected mice were cleared of infection. When measured at eight weeks after the last immunization, 67% of the infected mice were cleared of infection. None of the sham immunized mice were cleared of infection when measured at either 2.5 or eight weeks after the last immunization. The significance of the reduction in the percentage of mice cleared of infection when measured at eight weeks as compared to 2.5 weeks after the last immunization is unclear at present.

TABLE 11

| Mouse No. | Urease Test | Total anti-ureB Igs in Blood | Total IgAs in Feces | ureB IgA's in Feces | ure B IgA's in Feces/ Total IgA's in Feces |
|---|---|---|---|---|---|
| Ex. 4: | | | | | |
| 8 | 0.51 | 0.27 | 0.77 | 0.05 | 0.06 |
| 9 | 0.48 | 0.23 | 0.65 | 0.02 | 0.03 |
| 10 | 0.61 | 0.25 | 0.43 | 0.08 | 0.18 |
| 11 | 0.44 | 0.36 | 0.69 | 0.03 | 0.04 |
| 12 | 0.51 | 0.31 | 0.58 | 0.00 | 0.00 |
| 13 | 0.48 | 0.32 | 0.67 | 0.11 | 0.17 |
| 14 | 0.44 | 0.27 | 0.51 | 0.03 | 0.05 |
| 15 | 0.58 | 0.29 | 0.82 | 0.07 | 0.08 |
| 16 | 0.48 | 0.30 | 0.77 | 0.18 | 0.23 |
| 17 | 0.53 | 0.30 | 0.53 | 0.09 | 0.18 |
| 18 | 0.36 | 0.22 | 0.51 | 0.00 | 0.00 |
| 19 | 0.01 | 0.47 | 0.62 | 0.47 | 0.75 |
| 20 | 0.43 | 0.35 | 0.57 | 0.15 | 0.26 |
| 21 | 0.07 | 0.25 | 0.64 | 0.11 | 0.17 |
| 22 | 0.39 | 0.27 | 0.50 | 0.15 | 0.30 |
| 23 | 0.10 | 0.27 | 1.08 | ND | ND |
| 24 | 0.38 | 0.28 | 0.66 | ND | ND |
| 25 | 0.06 | 0.28 | 0.53 | ND | ND |
| Ex. 5: | | | | | |
| 7 | 0.02 | 0.11 | 0.61 | 0.06 | 0.11 |
| 8 | 0.06 | 0.13 | 0.62 | 0.02 | 0.03 |
| 9 | 0.01 | 0.15 | 0.62 | 0.04 | 0.07 |
| 10 | 0.00 | 0.15 | 0.59 | 0.03 | 0.05 |
| 11 | 0.02 | 0.19 | 0.60 | 0.15 | 0.24 |
| 12 | 0.02 | 0.16 | 0.60 | 0.00 | −0.01 |
| 13 | 0.02 | 0.19 | 0.66 | 0.07 | 0.11 |
| 14 | 0.44 | 0.18 | 0.62 | 0.00 | 0.00 |
| 15 | 0.00 | 0.10 | 0.64 | 0.08 | 0.12 |
| 16 | 0.03 | 0.14 | 0.62 | 0.29 | 0.46 |
| 25 | 0.26 | 0.35 | 0.98 | 0.07 | 0.07 |
| 26 | 0.30 | 0.38 | 1.12 | 0.04 | 0.03 |
| 27 | 0.00 | 0.39 | 1.15 | 0.01 | 0.01 |
| 28 | 0.17 | 0.33 | 0.97 | 0.02 | 0.02 |
| 29 | N.D.* | 0.38 | 1.00 | 0.08 | 0.08 |
| 30 | 0.00 | 0.34 | 0.69 | 0.04 | 0.06 |
| 31 | 0.00 | 0.38 | 0.76 | 0.08 | 0.10 |
| 32 | 0.00 | 0.37 | 0.58 | 0.02 | 0.04 |
| 33 | 0.00 | 0.38 | 1.07 | 0.22 | 0.21 |
| 34 | 0.00 | 0.35 | 0.64 | 0.06 | 0.09 |

In Table 11, the mice that were treated with ure B, used in Examples 4 and 5, were evaluated for the antibody content of the blood and the feces. The mouse numbers used correspond to the numbers used in Tables 8 and 9. The urease test results correspond to the results reported in Tables 8 and 9. "ND*" indicates that no data was available because one of the stomachs, from mice numbered 18–21, was lost. The inventors are unable to determine which of the sets of data from mice numbered 18–21 is incomplete. Therefore, the "ND" is not meant to be specifically assigned to mouse number 21.

In the assays of the mice from Example 4, and the mice numbered 1–10 from Example 5, the inventors had difficulty obtaining adequate samples for analysis.

The clearance of *H. felis* infection by oral administration of the *Helicobacter pylori* ure B subunit was not expected and is therefore novel. The results described herein also teach that the ure B subunit can be used to treat Helicobacter infection.

One skilled in the art will readily appreciate that the present invention is well adapted to carry out the objects and obtain the ends and advantages mentioned, as well as those inherent therein. The urease peptides, mucosal adjuvants, carriers, and antibodies, along with the methods, procedures, treatments, and assays, are exemplary and are not intended as limitations on the scope of the invention. Changes therein and other uses will occur to those skilled in the art which are encompassed within the spirit of the invention as defined by the scope of the claims.

We claim:

1. A method of treating Helicobacter infection in a mammal, said method comprising administering to a mucosal surface of said mammal a therapeutically effective amount of a purified polypeptide comprising an A subunit of a naturally occurring Helicobacter urease.

2. The method of claim 1, wherein said mammal is a human.

3. The method of claim 1, wherein said Helicobacter urease is *Helicobacter pylori* urease.

4. The method of claim 1, wherein said mucosal surface is oral.

5. The method of claim 1, wherein said mucosal surface is intranasal or rectal.

6. The method of claim 1, wherein said polypeptide is administered to said mammal in a dosage ranging from 100 µg to 1 g.

7. The method of claim 1, wherein said polypeptide is administered for a primary immunization schedule of three to eight times over one month.

8. The method of claim 1, wherein said polypeptide is administered to said mammal in association with a mucosal adjuvant.

9. The method of claim 8, wherein said mucosal adjuvant is selected from the group consisting of procholeragenoid; cholera toxin B subunit; fungal polysaccharides, including schizophyllan; muramyl dipeptide; muramyl dipeptide derivatives; phorbol esters; liposomes; microspheres; non-*Helicobacter pylori* bacterial lysate; labile toxin of *Escherichia coli*; block polymers; saponins; and ISCOMS.

10. The method of claim 8, wherein said mucosal adjuvant is a polypeptide of the labile toxin of *Escherichia coli*.

11. The method of claim 10, wherein said polypeptide of said toxin comprises the B subunit of said toxin.

12. The method of claim 8, wherein said polypeptide is genetically or chemically linked to said mucosal adjuvant.

13. The method of claim 12, wherein said mucosal adjuvant is the B subunit of cholera toxin.

14. The method of claim 1, wherein said polypeptide is administered in association with a carrier, in particulate form.

15. The method of claim 14, wherein said carrier is hydroxyapatite.

16. The method of claim 1, wherein said polypeptide is administered in association with a microsphere carrier.

17. The method of claim 16, wherein said microsphere carrier is a polylactide-coglycolide biodegradable microsphere carrier.

18. The method of claim 1, wherein said composition comprises a recombinant, live vector or a recombinant carrier system that expresses said polypeptide.

19. The method of claim 18, wherein said live vector is selected from the group consisting of *Salmonella typhimuriuim*, *Salmonella typhi*, Shigella, Bacillus, Lactobacillus, BCG, *Escherichia coli*, *Vibrio cholerae*, Campylobacter, yeast, Herpes virus, Adenovirus, Polio virus, Vaccinia virus, and Avipox.

20. The method of claim 18, wherein said carrier system is selected from the group consisting of Bluetongue virus-like particles, Rotavirus virus-like particles, and Ty particles.

21. A method of treating Helicobacter infection in a mammal, said method comprising administering to a mucosal surface of said mammal a therapeutically effective amount of a purified polypeptide comprising a B subunit of a naturally occurring Helicobacter urease.

22. The method of claim 21, wherein said mammal is a human.

23. The method of claim 21, wherein said Helicobacter urease is *Helicobacter pylori* urease.

24. The method of claim 21, wherein said mucosal surface is oral.

25. The method of claim 21, wherein said mucosal surface is intranasal or rectal.

26. The method of claim 21, wherein said polypeptide is administered to said mammal in a dosage ranging from 100 µg to 1 g.

27. The method of claim 21, wherein said polypeptide is administered for a primary immunization schedule of three to eight times over one month.

28. The method of claim 21, wherein said polypeptide is administered to said mammal in association with a mucosal adjuvant.

29. The method of claim 28, wherein said mucosal adjuvant is selected from the group consisting of procholeragenoid; cholera toxin B subunit; fungal polysaccharides, including schizophyllan; muramyl dipeptide; muramyl dipeptide derivatives; phorbol esters; liposomes; microspheres; non-*Helicobacter pylori* bacterial lysate; labile toxin of *Escherichia coli*; block polymers; saponins; and ISCOMS.

30. The method of claim 28, wherein said mucosal adjuvant is a polypeptide of the labile toxin of *Escherichia coli*.

31. The method of claim 30, wherein said polypeptide of said toxin comprises the B subunit of said toxin.

32. The method of claim 28, wherein said polypeptide is genetically or chemically linked to said mucosal adjuvant.

33. The method of claim 32, wherein said mucosal adjuvant is the B subunit of cholera toxin.

34. The method of claim 21, wherein said polypeptide is administered in association with a carrier, in particulate form.

35. The method of claim 34, wherein said carrier is hydroxyapatite.

36. The method of claim 21, wherein said polypeptide is administered in association with a microsphere carrier.

37. The method of claim 36, wherein said microsphere carrier is a polylactide-coglycolide biodegradable microsphere carrier.

38. The method of claim 21, wherein said composition comprises a recombinant, live vector or a recombinant carrier system that expresses said polypeptide.

39. The method of claim 38, wherein said live vector is selected from the group consisting of *Salmonella typhimurium*, *Salmonella typhi*, Shigella, Bacillus, Lactobacillus, BCG, *Escherichia coli, Vibrio cholerae*, Campylobacter, yeast, Herpes virus, Adenovirns, Polio virus, Vaccinia virus, and Avipox.

40. The method of claim 38, wherein said carrier system is selected from the group consisting of Bluetongue virus-like particles, Rotavirus virus-like particles, and Ty particles.

41. A vaccine composition consisting essentially of a polypeptide comprising an A subunit of a naturally occurring Helicobacter urease, and a mucosal adjuvant.

42. The vaccine composition of claim 41, wherein said Helicobacter urease is *Helicobacter pylori* urease.

43. The vaccine composition of claim 41, wherein said Helicobacter urease is *Helicobacter felis* urease.

44. The vaccine composition of claim 41, wherein said mucosal adjuvant is selected from the group consisting of procholeragenoid; cholera toxin B subunit; fungal polysaccharides, including schizophyllan; muramyl dipeptide; muramyl dipeptide derivatives; phorbol esters; liposomes; microspheres; non-*Helicobacter pylori* bacterial lysate; labile toxin of *Escherichia coli*; block polymers; saponins; and ISCOMS.

45. The vaccine composition of claim 41, wherein said polypeptide is genetically or chemically linked to said mucosal adjuvant.

46. The vaccine composition of claim 45, wherein said mucosal adjuvant is cholera toxin B subunit.

47. The vaccine composition of claim 41, further comprising a carrier, such that the composition can be delivered in particulate form.

48. The vaccine composition of claim 47, wherein said carrier is hydroxyapatite.

49. The vaccine composition of claim 41, further comprising a microsphere carrier.

50. The vaccine composition of claim 49, wherein said microsphere carrier is a polylactide-coglycolide biodegradable microsphere carrier.

51. The vaccine composition of claim 41, wherein said composition comprises a recombinant live vector or a recombinant carrier system that expresses said polypeptide.

52. The vaccine composition of claim 51, wherein said live vector is selected from the group consisting of *Salmonella typhhimurium, Salmonella typhi*, Shigella, Bacillus, Lactobacillus, BCG, *Escherichia coli, Vibrio cholerae*, Campylobacter, yeast, Herpes virus, Adenovirus, Polio virus, Vaccinia virus, and Avipox.

53. The vaccine composition of claim 51, wherein said carrier system is selected from the group consisting of Bluetongue virus-like particles, Rotaviius virus-like particles, and Ty particles.

54. A vaccine composition comprising a purified polypeptide comprising an A subunit of a naturally occurring Helicobacter urease, and a polypeptide of the labile toxin of *Escherichia coli*.

55. The vaccine composition of claim 54, wherein said polypeptide of said toxin comprises the B subunit of said toxin.

56. A vaccine composition consisting essentially of a polypeptide comprising a B subunit of a naturally occurring Helicobacter urease, and a mucosal adjuvant.

57. The vaccine composition of claim 56, wherein said Helicobacter urease is *Helicobacter pylori* urease.

58. The vaccine composition of claim 56, wherein said Helicobacter urease is *Helicobacter felis* urease.

59. The vaccine composition of claim 56, wherein said mucosal adjuvant is selected from the group consisting of procholeragenoid; cholera toxin B subunit; fungal polysaccharides, including schizophyllan; muramyl dipeptide; muramyl dipeptide derivatives; phorbol esters; liposomes; microspheres; non-*Helicobacter pylori* bacterial lysate; labile toxin of *Escherichia coli*; block polymers; saponins; and ISCOMS.

60. The vaccine composition of claim 56, wherein said polypeptide is genetically or chemically linked to said mucosal adjuvant.

61. The vaccine composition of claim 60, wherein said mucosal adjuvant is cholera toxin B subunit.

62. The vaccine composition of claim 56, further comprising a carrier, such that the composition can be delivered in particulate form.

63. The vaccine composition of claim 62, wherein said carnier is hydroxyapatite.

64. The vaccine composition of claim 56, further comprising a microsphere carrier.

65. The vaccine composition of claim 64, wherein said microsphere carrier is a polylactide-coglycolide biodegradable microsphere carrier.

66. The vaccine composition of claim 56, wherein said composition comprises a recombinant live vector or a recombinant carrier system that expresses said polypeptide.

67. The vaccine composition of claim 66, wherein said live vector is selected from the group consisting of *Salmonella typhiniurium, Salmonella typhi*, Shigella, Bacillus, Lactobacillus, BCG, *Escherichia coli, Vibrio cholerae*, Campylobacter, yeast, Herpes virus, Adenovirus, Polio virus, Vaccinia virus, and Avipox.

68. The vaccine composition of claim 66, wherein said carrier system is selected from the group consisting of Bluetongue virus-like particles, Rotavirus virus-like particles, and Ty particles.

69. A vaccine composition comprising a purified polypeptide comprising a B subunit of a naturally occurring Helicobacter urease, and a polypeptide of the labile toxin of *Escherichia coli*.

70. The vaccine composition of claim 69, wherein said polypeptide of said toxin comprises the B subunit of said toxin.

71. A method of preventing Helicobacter infection in a mammal, said method comprising administering to said mammal a prophylactically effective amount of the vaccine composition of claim 54.

72. A method of preventing Helicobacter infection in a mammal, said method comprising administering to said mammal a prop prophylactically effective amount of the vaccine composition of claim 69.

* * * * *

UNITED STATES PATENT AND TRADEMARK OFFICE
CERTIFICATE OF CORRECTION

PATENT NO. : 6,290,962 B1
DATED : September 18, 2001
INVENTOR(S) : Pierre Michetti, Irene Corthesy-Theulaz, Andre Blum, Catherine Davin, Rainer Haas, Jean-Pierre Kraehenbuhl and Emilia Saraga It is certified that error appears in the above-identified patent and that said Letters Patent is hereby corrected as shown below:

Title page,
Item [75], Inventors, replace "Rainier Haas," with -- Rainer Haas --;
Item [56], OTHER PUBLICATIONS, within the Weltzin et al. reference page numbers, replace "2775-782" with -- 2775-2782 --;
Within the Weltzin et al. reference journal title, replace "Injection" with -- Infection --;
Within the Solnick et al. reference page numbers, replace "2560-565" with -- 2560-2565 --;
Within the Davin et al. reference journal title, replace "*H. Pylor*" with -- *H. Pylori* --;
Within the Davin et al. reference journal title, replace "*H. felisinfection*" with -- *H. Felis infection* --;
Within the Ferrero et al. reference journal title, replace "*Helicobacter*spp:" with -- *Helicobacter* spp: --;
Within the Michetti et al. reference journal title, replace "*felis*Infection" with -- *felis* Infection -- and "*pylori*Urease," with -- *pylori* Urease, --;
Within the Michetti et al. reference journal name, replace "Gastroenterolgy" with -- Gastroenterology --;
Within the Isaacson et al. reference title, replace "Pathegenes is" with -- Pathogenesis --;
Within the Schmitt et al. reference title, replace "-lactode-c-o-" with -- lactide-co --;
Within the Sobala et al. reference title, replace "Nitrute" with -- Nitrate --; replace "Compound" with -- Compounds --; replace "total" with -- Total --; and replace "Carecinogenesis" with -- Carcinogenesis --;
Primary Examiner, replace "Mannfield" with -- Minnifield --;

Column 1,
Line 20, replace "cancer.4" with -- cancer. --;
Line 43, replace "elationship" with -- relationship --;

Column 4,
Line 19, replace "*Morcanella*" with -- *Morganella* --;
Line 26, replace "H. *fells*" with -- H. *felis* --;
Line 53, replace "glutaral-dehyde" with -- glutaraldehyde --;

Column 5,
Line 64, replace "*Oct.*" with -- Oct. --;

Column 9,
Line 9, replace "in a" with -- in an --;
Line 49, the words "Commercially available" should start a new paragraph;

UNITED STATES PATENT AND TRADEMARK OFFICE
CERTIFICATE OF CORRECTION

PATENT NO. : 6,290,962 B1
DATED : September 18, 2001
INVENTOR(S) : Pierre Michetti, Irene Corthesy-Theulaz, Andre Blum, Catherine Davin, Rainer Haas, Jean-Pierre Kraehenbuhl and Emilia Saraga It is certified that error appears in the above-identified patent and that said Letters Patent is hereby corrected as shown below:

Column 10,
Line 48, replace "Helicobacter pylori" with -- *Helicobacter pylori* --;

Column 11,
Line 45, replace "Effectivess" with -- Effectiveness --;

Column 13,
Line 61, replace "vector. for" with -- vector. For --;

Column 14,
Line 26, the words -- While not being bound by any theory, the -- should start a new paragraph;
Line 45, replace "*H. fells.*" with -- *H. felis.* --;

Column 16,
Line 53, replace "0.250%" with -- 0.25% --;

Column 18,
Line 49, replace "surfa ce" with -- surface --;

Column 24,
Line 8, within Table 4, replace "mice no" with -- mice no. --;

Column 27,
Line 50, replace "consisting on" with -- consisting of --;
Line 53, replace "Ouantification" with -- Quantification --;

Column 28,
Line 47, replace "of purified of" with -- of purified --;

Column 30,
Line 50, the words -- At day 70 all mice were sacrificed -- should start a new paragraph;

Column 31,
Line 31, replace "subsesequent" with -- subsequent --;
Line 46, replace "ureB" with -- ure B --;

UNITED STATES PATENT AND TRADEMARK OFFICE
CERTIFICATE OF CORRECTION

PATENT NO. : 6,290,962 B1
DATED : September 18, 2001
INVENTOR(S) : Pierre Michetti, Irene Corthesy-Theulaz, Andre Blum, Catherine Davin, Rainer Haas, Jean-Pierre Kraehenbuhl and Emilia Saraga It is certified that error appears in the above-identified patent and that said Letters Patent is hereby corrected as shown below:

Column 32,
Line 27, replace "termperature" with -- temperature --;

Column 37,
Line 51, replace "*typhhimurium*," with -- *typhimurium*, --;
Line 57, replace "Rotaviius" with -- Rotavirus --;

Column 38,
Line 39, replace "*typhiniurium*" with -- *typhimurium* --;
Line 60, delete "prop".

Signed and Sealed this

Third Day of September, 2002

Attest:

JAMES E. ROGAN
Attesting Officer    Director of the United States Patent and Trademark Office

UNITED STATES PATENT AND TRADEMARK OFFICE
CERTIFICATE OF CORRECTION

PATENT NO. : 6,290,962 B1  Page 1 of 1
DATED : September 18, 2001
INVENTOR(S) : Pierre Michetti et al.

It is certified that error appears in the above-identified patent and that said Letters Patent is hereby corrected as shown below:

<u>Title page,</u>
Item [73], Assignee, should read as follows:
-- [73]  Assignee: Ora Vax Merieux Co. --.

Signed and Sealed this

Ninth Day of December, 2003

JAMES E. ROGAN
*Director of the United States Patent and Trademark Office*